United States Patent
Matsuda

(10) Patent No.: US 8,820,165 B2
(45) Date of Patent: Sep. 2, 2014

(54) ULTRASONIC SENSOR AND ELECTRONIC DEVICE

(75) Inventor: Hiroshi Matsuda, Gifu (JP)

(73) Assignee: Seiko Epson Corporation, Tokyo (JP)

( * ) Notice: Subject to any disclaimer, the term of this patent is extended or adjusted under 35 U.S.C. 154(b) by 614 days.

(21) Appl. No.: 13/085,625

(22) Filed: Apr. 13, 2011

(65) Prior Publication Data

US 2011/0252890 A1  Oct. 20, 2011

(30) Foreign Application Priority Data

Apr. 14, 2010 (JP) ................. 2010-092929
Mar. 11, 2011 (JP) ................. 2011-054236

(51) Int. Cl.
*G01N 29/26* (2006.01)
*G01N 29/24* (2006.01)
*B06B 1/06* (2006.01)

(52) U.S. Cl.
CPC .............. *G01N 29/24* (2013.01); *B06B 1/0629* (2013.01)
USPC .............................................. 73/632; 73/627

(58) Field of Classification Search
USPC ............ 73/627, 596, 632, 641; 310/324, 338, 310/339
See application file for complete search history.

(56) References Cited

U.S. PATENT DOCUMENTS

| | | | | |
|---|---|---|---|---|
| 4,412,316 A | * | 10/1983 | Diepers | 367/105 |
| 4,747,192 A | * | 5/1988 | Rokurota | 29/25.35 |
| 5,160,870 A | * | 11/1992 | Carson et al. | 310/339 |
| 5,406,163 A | * | 4/1995 | Carson et al. | 310/334 |
| 6,515,402 B2 | * | 2/2003 | Klee et al. | 310/324 |
| 7,230,368 B2 | * | 6/2007 | Lukacs et al. | 310/335 |
| 7,830,069 B2 | * | 11/2010 | Lukacs et al. | 310/334 |
| 8,183,745 B2 | * | 5/2012 | Trolier-McKinstry et al. | 310/334 |

FOREIGN PATENT DOCUMENTS

| | | |
|---|---|---|
| EP | 1629778 A1 | 3/2006 |
| JP | 2003-524907 A | 8/2003 |
| JP | 2006-061252 A | 3/2006 |
| WO | 99/56500 A1 | 11/1999 |

* cited by examiner

*Primary Examiner* — J M Saint Surin
(74) *Attorney, Agent, or Firm* — Global IP Counselors, LLP

(57) ABSTRACT

The ultrasonic sensor has a plurality of ultrasonic transducers disposed two-dimensionally on a sensor substrate. The sensor substrate is divided into areas by an X axis and a Y axis which intersect one another in plan view looking at the sensor substrate along the thickness direction. In each of the areas, each of the lower electrode lines which leads out from the lower electrode of each of the ultrasonic transducers has a linear segment which extends in a direction away from the substrate center point where the X axis and Y axis intersect.

18 Claims, 13 Drawing Sheets

ULTRASONIC SENSOR AND ELECTRONIC DEVICE

CROSS-REFERENCE TO RELATED APPLICATIONS

This application claims priority to Japanese Patent Application No. 2010-092929 filed on Apr. 14, 2010 and Japanese Patent Application No. 2011-054236 filed on Mar. 11, 2011. The entire disclosure of Japanese Patent Application Nos. 2010-092929 and 2011-054236 is hereby incorporated herein by reference.

BACKGROUND

1. Technical Field

The present invention relates to an ultrasonic sensor and to an electronic device.

2. Related Art

Ultrasonic endoscopes having a two-dimensional array structure in which ultrasonic transducers, used for sending and receiving ultrasound, are disposed in matrix form, are known in the prior art (for example, see Japanese Laid-Open Patent Application Publication No. 2006-61252).

More specifically, the ultrasonic transducers disclosed in Japanese Laid-Open Patent Application Publication No. 2006-61252 are composed of a piezoelectric element sandwiched between an individual electrode and a common electrode. The ultrasonic transducers are disposed respectively aligned in semicircles along the circumferential direction and the width direction.

According to Japanese Laid-Open Patent Application Publication No. 2006-61252, twelve sets of arrays, each of which contains ultrasonic transducers disposed in fifteen rows in the circumferential direction and five columns in the width direction, are disposed along the circumferential direction. In this configuration, signal lines provided as electrode lines lead out along the circumferential direction from the individual electrodes of the ultrasonic transducers in each row. The signal lines that lead out from the individual electrodes all extend in a single direction along the circumferential direction.

SUMMARY

Because the signal lines that lead out from the individual electrodes in the ultrasonic transducers of Japanese Laid-Open Patent Application Publication No. 2006-61252 all extend in a single direction along the circumferential direction, fifteen signal lines are disposed between each column.

In situations where large numbers of ultrasonic transducers, for example, fifteen or more, are disposed in this way, the number of signal lines leading out between columns equals the number of ultrasonic transducers disposed therein. However, space between columns is limited, so in situations where a large number of ultrasonic transducers are disposed, increased complexity of the signal lines which are routed through spaces between columns can be a problem.

It is accordingly an object of the present invention to provide an ultrasonic sensor and electronic device which have fewer numbers of electrode lines leading out from the electrodes between the ultrasonic transducers.

An ultrasonic sensor according to a first aspect includes a sensor substrate, a plurality of ultrasonic transducers and a plurality of first electrode lines. The sensor substrate has a plurality of areas divided by at least two hypothetical dividing lines that intersect one another in plan view looking at the sensor substrate in a thickness direction. The ultrasonic transducers are disposed two-dimensionally on the sensor substrate, each of the ultrasonic transducers having a first electrode. The first electrode lines have as origins thereof the first electrodes of the ultrasonic transducers, each of the first electrode lines having a linear segment extending, within each of the areas of the sensor substrate, in a direction away from an intersection point between the hypothetical dividing lines.

According to the first aspect, the sensor substrate is provided with a plurality of areas divided by at least two hypothetical dividing lines which intersect one another. Within each area, first electrode lines that are routed from origins at first electrodes included in the ultrasonic transducers have a linear segment that extends in a direction away from the intersection point of the hypothetical dividing lines.

According to this feature, within each area, the first electrode lines have linear segments that extend in a direction away from the intersection point and that therefore do not cross over the hypothetical dividing lines and lead out towards other areas. Specifically, the sensor substrate is divided into a plurality of areas by the hypothetical dividing lines, and within each of the areas, the first electrode lines lead out from the first electrodes in such a way that there is no crossing over between areas. Consequently, the number of first electrode lines that lead out between ultrasonic transducers within the areas can be reduced as compared with situations where the sensor substrate is not divided and where the first electrode lines lead out in the same direction exclusively, as in the prior art.

In the ultrasonic sensor, in preferred practice, the linear segment of each of the first electrode lines within each of the areas extends along a prescribed direction.

According to this aspect, the linear segments of the first electrode lines extend along a prescribed direction within each area, and therefore the lines can be disposed substantially parallel to one another. For this reason, in situations where, for example, the plurality of ultrasonic transducers are disposed in a two-dimensional matrix pattern, the linear segment of each of the first electrode lines can be disposed along the ultrasonic transducer alignment direction, whereby the wiring can be disposed uniformly between the ultrasonic transducers. For this reason, design of line layout can be performed easily, and production of the ultrasonic transducers and first electrode lines can be performed easily as well.

In the ultrasonic sensor, in preferred practice, each of the first electrode lines has, between the ultrasonic transducers, a linear lead portion leading out from a corresponding one of the first electrodes of the ultrasonic transducers, and a line portion corresponding to the linear segment, and extending from the lead portion along a straight line intersecting the lead portion.

According to this aspect, the first electrode lines are provided with lead portions and line portions, and therefore the line portions can be disposed at a location further away from the first electrode, by the equivalent of the length of the lead portions. For this reason, the lead portions that lead out from the first electrodes of the ultrasonic transducers lined up in one direction can be given respectively different lengths, whereby the line portions can be routed substantially parallel to one another along the one direction, design of line layout can be performed easily, and production of the ultrasonic transducers and first electrode lines can be performed easily as well.

In the ultrasonic sensor, in preferred practice, the at least two hypothetical dividing lines include a first hypothetical dividing line and a second hypothetical dividing line which intersect one another in plan view looking at the sensor substrate in the thickness direction, the ultrasonic transducers are two-dimensionally disposed in a direction parallel to the first hypothetical dividing line and a direction parallel to the second hypothetical dividing line, the sensor substrate includes four areas divided by the first hypothetical dividing line and the second hypothetical dividing line, and within each of the areas, the linear segment of each of the first electrode lines extends in the direction parallel to the first hypothetical dividing line.

In situations where the substrate is divided into four or more areas, the number of first electrode lines leading out between the ultrasonic transducers in each area can be further reduced. However, in a situation where, for example, a square sensor substrate divided into nine parts (3×3) is used, the area formed in the center section will be surrounded by the other areas. For this reason, the first electrode lines of the ultrasonic transducers disposed in the center section must inevitably cross over the hypothetical dividing lines and lead out into other areas. In such situations, because the first electrode lines cross the hypothetical dividing lines from the area in the center section and lead out into other areas, the number of first electrode lines leading out between the ultrasonic transducers in each area cannot be reduced even if the number of divided areas is increased.

According to this aspect, the sensor substrate is divided into four areas by two hypothetical dividing lines which intersect one another. Through quadripartite division in this manner, unlike a configuration having, for example, nine divisions as described above, there is no formation of an area in the center section, and the number of first electrode lines leading out between the ultrasonic transducers in each area can be reliably reduced, while complexity of lead out directions of the first electrode lines in association with an large number of divided areas can be avoided.

In the ultrasonic sensor, in preferred practice, the first hypothetical dividing line and the second hypothetical dividing line are orthogonal to one another.

Here, the first hypothetical dividing line can be set as the X axis and the second hypothetical dividing line as the Y axis. In this situation, the plurality of ultrasonic transducers are two-dimensionally disposed along the X axis and the Y axis, and the linear segments of the first electrode lines extend along the X axis.

According to this aspect, for example, in the two areas to either side of the second hypothetical dividing line (Y axis), the first electrode lines which extend along the first hypothetical dividing line (X axis) never cross the Y axis to lead out in the Y axis direction. Similarly, in the two areas to either side of the X axis, the first electrode lines which extend along the Y axis never cross the X axis to lead out in the X axis direction. Specifically, in each area, the number of first electrode lines leading out between the ultrasonic transducers can be reduced in an arrangement whereby none of the first electrode lines which lead out from the first electrodes cross over the X axis or Y axis respectively to lead out into other areas.

In the ultrasonic sensor, in preferred practice, each of the ultrasonic transducers has a second electrode, and in each of the areas, a second electrode line that interconnects at least two of the second electrodes extends in the direction parallel to the first hypothetical dividing line with the second electrode line being connected to a common electrode line disposed along the second hypothetical dividing line.

In the prior art configuration described previously, the lines that lead out from each of the common electrodes of each of the ultrasonic transducers are respectively connected to common electrode lines which are furnished to individual rows. Specifically, it is necessary to furnish each row with a common electrode line, and the large number of common electrode lines results in a complex structure.

According to this aspect, second electrode lines which extend in a direction along the first hypothetical dividing line respectively connect to the common electrode line, and this common electrode line is disposed along the second hypothetical dividing line only. Consequently, the number of common electrode lines can be greatly reduced as compared with the prior art configuration, and the configuration can be simpler.

Additionally, the first electrode lines extend in a direction along the first hypothetical dividing line and away from the point of intersection of the hypothetical dividing lines, while the common electrode line lies along the second hypothetical dividing line, whereby contact of the first electrode lines and the common electrode line may be prevented.

In the ultrasonic sensor, in preferred practice, the second electrode line extends linearly from each of the ultrasonic transducers in the direction parallel to the first hypothetical dividing line and interconnects each of the second electrodes of the ultrasonic transducers disposed in the direction parallel to the first hypothetical dividing line, and between each of the ultrasonic transducers, each of the first electrode lines have a lead portion leading out from a corresponding one of the first electrodes of the ultrasonic transducers in the direction parallel to the second hypothetical dividing line, and a line portion extending from the lead portion in the direction parallel to the first hypothetical dividing line.

According to this aspect, the lead portions of the first electrode lines lead out in a direction along the second hypothetical dividing line between each of the ultrasonic transducers, and the line portions extend from the distal ends of the lead portions in a direction along the first hypothetical dividing line. The second electrode lines extend linearly in a direction along the first hypothetical dividing line. According to this feature, by virtue of the lead portions, the line portions extend in a direction along the first hypothetical dividing line at locations away from the second electrode lines, and therefore do not intersect the second electrode lines. Consequently, shorting of the first electrodes and the second electrodes due to contact of the first electrode lines and the second electrode lines can be reliably prevented.

In the ultrasonic sensor, in preferred practice, the lead portion of each of the first electrode lines has an origin at the corresponding one of the first electrodes, and extends in a direction away from the first hypothetical dividing line.

Here, depending on the lead out direction of the lead portions of the first electrode lines, there is a risk that the lead portions will intersect the common electrode line which is disposed along the hypothetical dividing lines.

According to this aspect, the lead portions of the first electrode lines lead out in a direction away from the first hypothetical dividing line, and therefore even in a situation where the common electrode line is disposed along the second hypothetical dividing line, intersection of the lead portions and the common electrode line can be more reliably prevented.

The ultrasonic sensor, in preferred practice, further includes a common electrode line extending from an outside peripheral part of the sensor substrate along the first hypothetical dividing line to the intersection point of the first hypothetical dividing line and the second hypothetical dividing line. Also, in preferred practice, the sensor substrate includes four areas divided by the first hypothetical dividing line and the second hypothetical dividing line which intersect one another in plan view looking at the sensor substrate in the thickness direction, each of the ultrasonic transducers has a second electrode, and being disposed at a location on one of a plurality of concentric circles centered on the intersection point of the first hypothetical dividing line and the second hypothetical dividing line, each of the first electrode lines which leads out from the first electrode of each of the ultrasonic transducers extends, in each of the areas, to the outside peripheral part of the sensor substrate in a direction away from the intersection point of the first hypothetical dividing line and the second hypothetical dividing line, and each of the second electrode lines which leads out from the second electrode of each of the ultrasonic transducers extends to an area inward of an outermost one of the concentric circles, and has a linear segment that extends in a direction approaching the intersection point of the first hypothetical dividing line and the second hypothetical dividing line.

In this aspect, the ultrasonic transducers are disposed, for example, on three concentric circles. When doing this, the number of ultrasonic transducers disposed on each of the concentric circles is made equal to the number of areas. For example, going in order from smaller diameter, one ultrasonic transducer for each area, for a total of four, are disposed on the first concentric circle; two ultrasonic transducers for each area, for a total of eight, are disposed on the second concentric circle; and three ultrasonic transducers for each area, for a total of twelve, are disposed on the third concentric circle.

According to this aspect, the common electrode line is extended along the first hypothetical dividing line to the intersection, and the first electrode lines extended in a direction away from the intersection to the outside peripheral part of the sensor substrate. The second electrode lines are extended to areas to the inside of the outermost circle among the plurality of concentric circles, and have linear segments extending in a direction that approaches the intersection point of the first hypothetical dividing line and the second hypothetical dividing line.

Consequently, the first electrode lines and the second electrode lines may be disposed without intersecting one another. The first electrode lines can also connect to the common electrode line via the first electrode lines of other ultrasonic transducers, and routing of the lines may be performed easily.

In the ultrasonic sensor, in preferred practice, the intersection point of the at least two hypothetical dividing lines lies at a substantially central point of the sensor substrate in plan view looking at the sensor substrate in the thickness direction.

Here, the "approximate center point of the sensor substrate" can refer, in situations where the ultrasonic transducers are divided into an even number of parts and disposed in two directions, to the center point of the substrate; or in situations where the ultrasonic transducers are divided into an odd number of parts and disposed in two directions, to the point of intersection of two hypothetical dividing lines which diverge from the center point of the substrate, and is used herein to include both meanings.

According to this aspect, because the intersection point of the first hypothetical dividing line and second hypothetical line lie at the approximate center point of the sensor substrate, the sensor substrate can be divided into four approximately equal areas. In so doing, it is possible to minimize bias in the number of first electrode lines that are routed between ultrasonic transducers in individual areas, so these numbers can be made approximately the same. Consequently, whereas in situations where the size of each area differs appreciably it is necessary to respectively modify the width of spaces between the ultrasonic transducers in individual areas, because the number of lines in each of the areas is approximately the same, the production steps for disposing the ultrasonic transducers on the sensor substrate can be simpler.

An ultrasonic sensor according to another aspect includes a sensor substrate, a plurality of ultrasonic transducers, a common electrode line, a plurality of first electrode lines, and a plurality of second electrode lines. Each of the ultrasonic transducers has a first electrode and a second electrode and each of which being disposed two-dimensionally on the sensor substrate along a first direction and a second direction intersecting the first direction. The common electrode line is disposed along the first direction between columns of the ultrasonic transducers. The first electrode lines each has as an origin each of the first electrodes of the ultrasonic transducers. The second electrode lines interconnect the second electrodes of at least two of the ultrasonic transducers lined up in a direction parallel to the second direction. Each of the first electrode lines has a linear segment extending in the direction parallel to the second direction and extending in a direction away from the common electrode line. The second electrode lines extend along the second direction and connecting to the common electrode line.

According to this aspect, the ultrasonic transducers are disposed on the sensor substrate in a two-dimensional arrangement along a first direction and a second direction which intersect one another. The common electrode line is disposed along the first direction between columns of the ultrasonic transducers lying along the first direction, and the plurality of second electrode lines which interconnect the second electrodes of a plurality of ultrasonic transducers lying along the second direction extend along the second direction and connect to the common electrode line. Therefore, the second electrodes of the plurality of ultrasonic transducers which are disposed on the sensor substrate can connect to a single common electrode line via the plurality of second electrode lines. Consequently, if the sensor substrate is provided with a single terminal which is connected to the common electrode line, voltage can applied to the second electrodes, and the number of lines and terminals needed for the second electrodes can be minimized.

Each of the first electrode lines routed from origins at the first electrodes of the ultrasonic transducers lie along the second direction and has a linear segment which extends in a direction away from the common electrode line.

For this reason, the first electrode lines do not lead out across the common electrode line. Consequently, the number of first electrode lines led out between the ultrasonic transducers can be reduced, as compared to a situation where the first electrode lines lead out in the same direction only as in the prior art. Therefore, design of the line layout may be performed easily.

In the ultrasonic sensor, in preferred practice, each of the first electrode lines has a lead portion leading out in a direction parallel to the first direction from a corresponding one of the first electrodes of the ultrasonic transducers between each of the ultrasonic transducers, and a line portion corresponding to the linear segment, and extending from the lead portion along a straight line intersecting the lead portion.

According to this aspect, because the first electrode lines are provided with lead portions and with line portions, the line portions can be disposed at locations away from the first electrodes by the equivalent of the length of the lead portions. For this reason, by adopting respectively different lengths for the lead portions that lead out from the first electrodes of the ultrasonic transducers lined up in one direction, each of the line portions can be routed substantially parallel to one another along a straight line intersecting the lead portions, design of line layout can be performed easily, and production of the ultrasonic transducers and first electrode lines can be performed easily as well.

The ultrasonic sensor, in preferred practice, further includes a common electrode terminal connected to the common electrode line. In preferred practice, the second electrode lines are connected to the common electrode line at locations between a proximal end of the common electrode line connected to the common electrode terminal and a distal end of the common electrode line at an opposite side from the proximal end, and the lead portion leading out from each of the first electrodes of a first group extend away from a direction in which the lead portion leading out from each of the first electrodes of a second group extend, the first electrodes of the first group belonging to the ultrasonic transducers connected to a second group of the second electrode lines connected to the common electrode line at a location between a midpoint and the distal end of the common electrode line, the first electrodes of the second group belonging to the ultrasonic transducers connected to a second group of the second electrode lines connected to the common electrode line at a location between the midpoint and the proximal end of the common electrode line.

According to this aspect, at locations where the second electrode lines of the ultrasonic transducers connect to common electrode line, the plurality of ultrasonic transducers are separated into two groups, and the lead portions which lead from each of the first electrode lines of the ultrasonic transducers of each group lead out in directions away from one another, whereby the line layout of the first electrode lines can easily be designed to be symmetrical.

An ultrasonic sensor according to another aspect includes a sensor substrate, a plurality of ultrasonic transducers, a first common electrode line, and a second common electrode line. Each of the ultrasonic transducers has a first electrode and a second electrode, and each of the ultrasonic transducers is disposed two-dimensionally on the sensor substrate along a first direction and a second direction intersecting the first direction. The first common electrode line extends in a direction parallel to the first direction, and is disposed between columns of the ultrasonic transducers. The second common electrode line extends in a direction parallel to the second direction, is disposed between columns of the ultrasonic transducers, and being connected to the first common electrode line. At least one of a plurality of areas partitioned by the first common electrode line and the second common electrode line in plan view serves as a first line pattern area while the remaining area serving as a second line pattern area. In the first line pattern area, each of a plurality of first electrode lines has as origins thereof the first electrodes of the ultrasonic transducers having a linear segment extending in the direction parallel to the second direction and in a direction away from the first common electrode line, and a second electrode line interconnects the second electrodes of at least two of the ultrasonic transducers that line up in the direction parallel to the second direction extending in the direction parallel to the second direction and being connected to the first common electrode line. In the second line pattern area, each of a plurality of first electrode lines has as origins the first electrodes of the ultrasonic transducers having a linear segment extending in the direction parallel to the first direction and in a direction away from the second common electrode line, and a second electrode line interconnects the second electrodes of at least two of the ultrasonic transducers that line up in the direction parallel to the first direction extending in the direction parallel to the first direction and being connected to the second common electrode line.

According to this aspect, in the first line pattern area and the second line pattern area, the direction of extension of the linear segments of the first electrode lines differ between the first direction and the second direction. Therefore, the ultrasonic sensor can be designed with any of various line layouts.

In the ultrasonic sensor, in preferred practice, in the first line pattern area, each of the first electrode lines has a lead portion leading out from a corresponding one of the first electrodes of the ultrasonic transducers between the ultrasonic transducers in the direction parallel to the first direction, and a line portion corresponding to the linear segment, and extending from the lead portion along a straight line intersecting the lead portion, and in the second line pattern area, each of the first electrode lines has a lead portion leading out from a corresponding one of the first electrodes of the ultrasonic transducers between the ultrasonic transducers in the direction parallel to the second direction, and a line portion corresponding to the linear segment, and extending from the lead portion along a straight line intersecting the lead portion.

In this aspect, the direction of the lead portions and the line portions of the first electrode lines is different in the first line pattern area and the second line pattern area. Therefore, the ultrasonic sensor can be designed with any of various line layouts.

The ultrasonic sensor, in preferred practice, further includes a common electrode terminal connected to the first common electrode line. In preferred practice, the second common electrode line is connected to the first common electrode line at a point between a proximal end of the first common electrode line connected to the common electrode terminal, and a distal end of the first common electrode line at an opposite side from the proximal end, the lead portion leading out from each of the first electrodes of a first group extends away from a direction in which the lead portion leading out from each of the first electrodes of a second group extend, the first electrodes of the first group belonging to the ultrasonic transducers connected to the second electrode line connected to the first common electrode line at a location between the distal end and a point where the second common electrode line is connected to the first common electrode line, and the first electrodes of the second group belonging to the ultrasonic transducers connected to the second electrode line connected to the first common electrode line at a location between the proximal end and the point where the second common electrode line is connected to the first common electrode line.

According to this aspect, in the first line pattern area, the lead portions of the first electrode lines lead out from sections along the second electrode lines in a direction away from one another, whereby intersection of the first electrode lines of the first line pattern area and the second common electrode line can be prevented more reliably.

In the ultrasonic sensor, in preferred practice, the lead portion leading out from each of the first electrodes of a third group extends away from a direction in which the lead portion leading out from each of the first electrodes of a fourth group extend, the first electrodes of the third group belonging to the ultrasonic transducers connected to the second electrode line connected the second common electrode line at a location between one end of the second common electrode line and the point where the second common electrode line is connected to the first common electrode line, the first electrodes of the fourth group belonging to the ultrasonic transducers connected to the second electrode line connected to the second common electrode line at a location between another end of the second common electrode line and the point where the second common electrode line is connected to the first common electrode line.

According to this aspect, in the second line pattern area, the lead portions of the first electrode lines lead out from sections along the first electrode lines in a direction away from one another, whereby intersection of the first electrode lines of the second line pattern area and the first common electrode line can be prevented more reliably.

The electronic device of the present invention is characterized in comprising the ultrasonic sensor described previously.

In this aspect, by virtue of providing the ultrasonic sensor described previously, there can be realized an electronic device having the advantage that the number of electrode lines can be reduced.

BRIEF DESCRIPTION OF THE DRAWINGS

Referring now to the attached drawings which form a part of this original disclosure.

DETAILED DESCRIPTION OF EXEMPLARY EMBODIMENTS

First Embodiment

A first embodiment according to the present invention is described below on the basis of the drawings.

General Configuration of Ultrasonic Sensor

Figure 1:
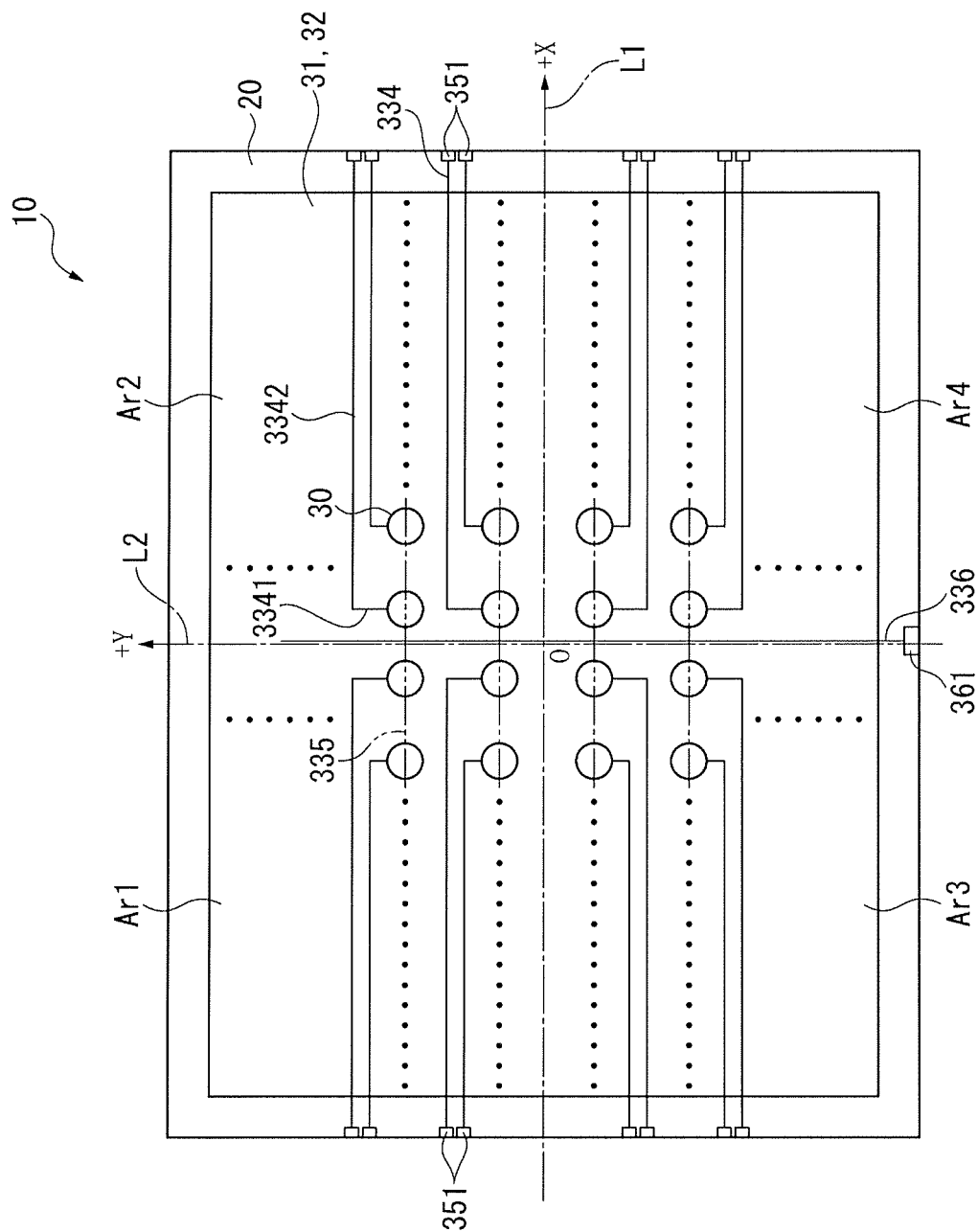
FIG. 1 is a plan view showing a general configuration of an ultrasonic sensor according to a first embodiment of the present invention.

FIG. 1 is a plan view showing a general configuration of an ultrasonic sensor 10 according to the present embodiment.

The ultrasonic sensor 10 is provided with a plurality of ultrasonic transducers 30 which are mounted on a sensor substrate 20. As shown in FIG. 1, the ultrasonic sensor 10 is configured in a two-dimensional array structure of matrix form in which the plurality of ultrasonic transducers 30 are disposed with uniform spacing along the horizontal direction (X axis L1) and the vertical direction (Y axis L2) on the sensor substrate 20. In the present embodiment, the vertical direction along the Y axis L2 is designated as the first direction, and the horizontal direction along the X axis L1 is designated as the second direction.

The sensor substrate 20 is formed with generally rectangular shape, and is formed of semiconductor-forming material such as silicon (Si), for example. Seen in plan view when looking at the substrate 20 in the thickness direction, this sensor substrate 20 has four areas (a first area Ar1, a second area Ar2, a third area Ar3, and a fourth area Ar4) which are divided by the X axis L1 (first hypothetical dividing line) and the Y axis L2 (second hypothetical dividing line), which pass through the substrate center point O (intersection point, approximate substrate center point) and are orthogonal to one another.

Configuration of Ultrasonic Transducers

Figure 2:
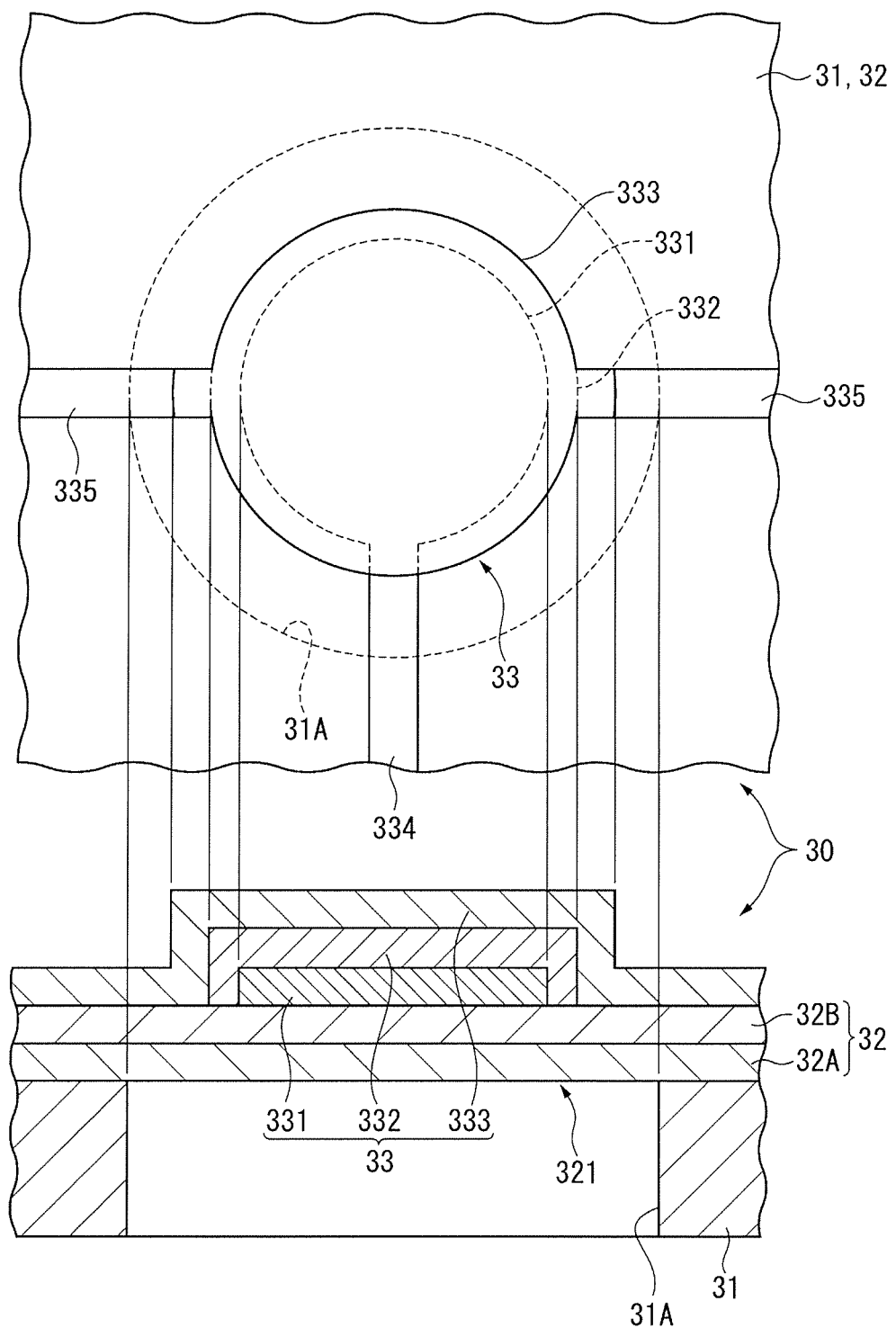
FIG. 2 is a plan view and cross sectional view showing an ultrasonic transducer according to the first embodiment.

The general configuration of the ultrasonic transducers 30 is described here. FIG. 2 is a plan view and a cross sectional view of the general configuration of an ultrasonic transducer 30 according to the present embodiment.

Figure 4:
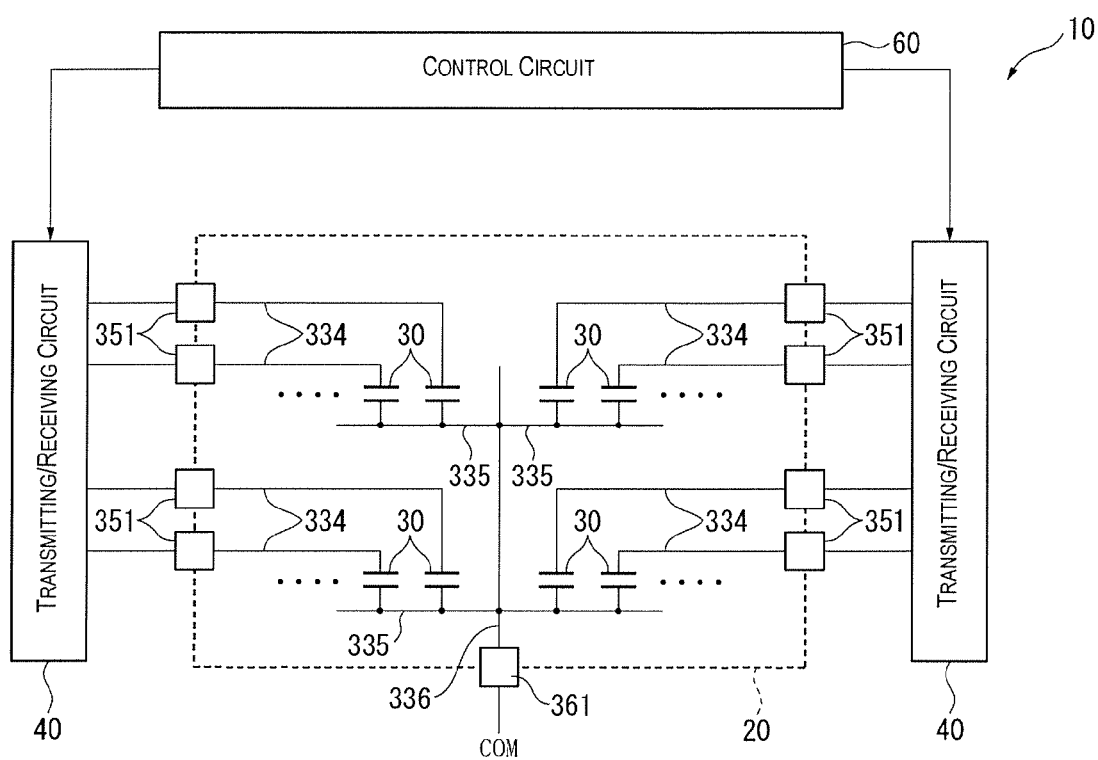
FIG. 4 is a circuit diagram of the ultrasonic sensor according to the first embodiment.

The ultrasonic transducer 30 is an element which is adapted to transmit ultrasound on the basis of a signal from a transmitting/receiving circuit 40 shown in FIG. 4; the element is also adapted to receive ultrasound reflected from a sensed object or the like, and covert the ultrasound to an electrical signal for output to the transmitting/receiving circuit 40.

As shown in FIG. 2, the ultrasonic transducer 30 is provided with a support 31 with an aperture 31A formed therein, a support film 32 disposed covering the top of the support 31 and closing off the aperture 31A, and a piezoelectric body 33 formed over the support film 32.

The support 31 is a section that is formed at a location where the ultrasonic transducer 30 is to be disposed on the sensor substrate 20. The aperture 31A formed in the support 31 is formed with circular shape in plan view, for example. In so doing, in a diaphragm 321 which is constituted by the support film 32 to the inside of the aperture 31A, stress arising in response to flexion of the diaphragm 321 can be made uniform.

The support film 32 is formed over the support 31 in a condition such that the aperture 31 is closed off. The support film 32 is composed, for example, of a two-layer structure of an $SiO_2$ layer 32A and a $ZrO_2$ layer 32B. In a situation where the support 31 is an Si substrate, the $SiO_2$ layer 32A can be formed through a thermal oxidation process carried out on the substrate surface. The $ZrO_2$ layer 32B can be formed over the $SiO_2$ layer 32A by a procedure such as sputtering, for example. In a situation where, for example, PZT (lead zirconate titanate) is used for the piezoelectric film 332, the $ZrO_2$ layer 32B may serve as a layer for preventing the Pb making up the PZT from diffusing into the $SiO_2$ layer 32A. The $ZrO_2$ layer 32B also has the effect of improving flexion efficiency in response to strain of the piezoelectric body 33.

The piezoelectric body 33 is provided with a lower electrode 331 (first electrode) stacked on the upper layer of the support film 32, a piezoelectric film 332 formed over the lower electrode 331, and an upper electrode 333 (second electrode) formed over the piezoelectric film 332.

As shown in FIGS. 1 and 2, a lower electrode line 334 (first electrode line) leads out from the lower electrode 331 and follows along the Y axis direction over the top of the support film 32. An upper electrode line 335 (second electrode line) leads out from the upper electrode 333 and follows along the X axis direction over the top of the support film 32.

The piezoelectric film 332 is formed, for example, through deposition of PZT. While PZT is used for the piezoelectric film 332 in the present embodiment, any material may be used as long as the material is capable of contracting in an in-plane direction in response to application of voltage, examples being lead titanate (PbTiO$_3$), lead zirconate (PbZrO$_3$), lead lanthanum titanate ((Pb, La)TiO$_3$), and the like.

In this ultrasonic transducer 30, the piezoelectric film 332 expands and contracts in an in-plane direction through application of voltage to the lower electrode 331 and to the upper electrode 333. At this time, the support film 32 is joined via the lower electrode 331 to one face of the piezoelectric film 332. While the upper electrode 333 has been formed at the other face of the piezoelectric film 332, no additional layers are stacked over the upper electrode 333. Consequently, the piezoelectric film 332 resists expansion and contraction at the support film 32 side thereof, while readily expanding and contracting at the upper electrode 333 side. Therefore, when voltage is applied to the piezoelectric film 332, flexion giving rise to convexity towards the aperture 31A side arises and induces flexion of the diaphragm 321. Consequently, through application of AC voltage to the piezoelectric film 332, the diaphragm 321 oscillates in the film thickness direction, and ultrasound is output due to this oscillation of the diaphragm 321.

Also, in the ultrasonic transducer 30, when ultrasound reflected from a sensed object is received by the diaphragm 321, the diaphragm 321 oscillates in the film thickness direction. Through this oscillation of the diaphragm 321, in the ultrasonic transducer 30 a potential difference arises between the face of the piezoelectric film 332 on the lower electrode 331 side thereof and the face on the upper electrode 33 side, and an electrical signal (current) dependent on the amount of displacement of the piezoelectric film 332 is output from the upper electrode 333 and the lower electrode 331.

Placement Configuration of Ultrasonic Transducers

Figure 3:
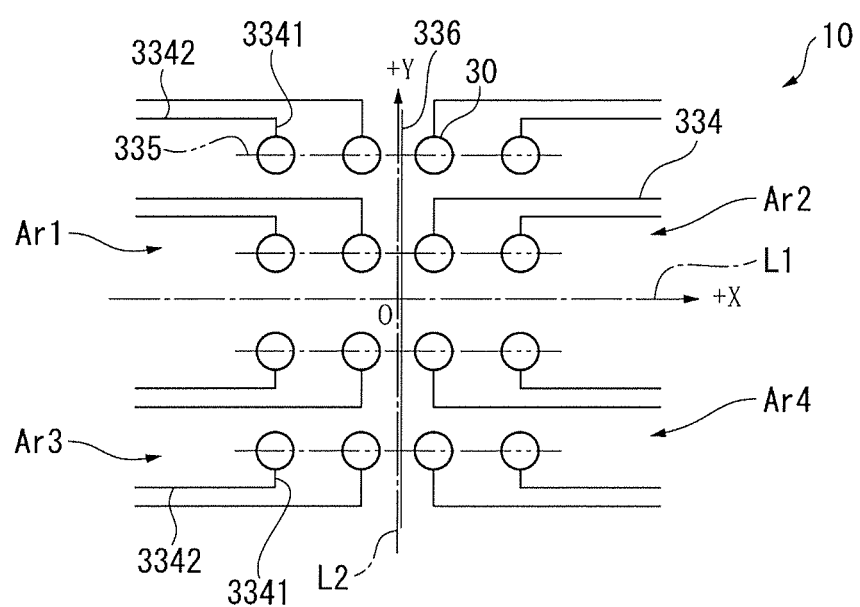
FIG. 3 is an enlarged plan view showing line construction of an ultrasonic transducer according to the first embodiment.

FIG. 3 is a plan view of line construction of an ultrasonic transducer 30, showing an enlarged portion of the ultrasonic sensor 10 shown in FIG. 1.

In the first area Ar1, the lower electrode lines 334 which lead out from the lower electrode 331 of each of the ultrasonic transducers 30 are provided with lead portions 3341 extending towards the +Y direction side along the Y axis L2 (a direction parallel to the second hypothetical dividing line) from the lower electrode 331, and with line portions 3342 extending towards the −X direction side along the X axis L1 (a direction parallel to the first hypothetical dividing line) from the distal end of the lead 3341.

In the second area Ar2, the lower electrode lines 334 are provided with lead portions 3341 extending towards the +Y direction side along the Y axis L2 (a direction parallel to the second hypothetical dividing line), and with line portions 3342 extending towards the +X direction side along the X axis L1 (a direction parallel to the first hypothetical dividing line) from the distal end of the lead 3341.

In the first area Ar1 and the second area Ar2, the lead portions 3341 of the lower electrode lines 334 respectively lead out in a direction away from the X axis L1, but in situations where, unlike the present embodiment, the common electrode line 336 (discussed later) is not formed along the X axis L1, optionally, the lead portions 3341 may lead out towards the X axis L1.

In the third area Ar3, the lower electrode lines 334 are provided with lead portions 3341 extending towards the −Y direction side along the Y axis L2, and with line portions 3342 extending towards the −X direction side along the X axis L1 from the distal end of the lead 3341.

In the fourth area Ar4, the lower electrode lines 334 are provided with lead portions 3341 extending towards the −Y direction side along the Y axis L2, and with line portions 3342 extending towards the +X direction side along the X axis L1 from the distal end of the lead 3341.

The upper electrode lines 335 connect the upper electrodes 33 of each of the ultrasonic transducers 30 to one another, and extend in linear fashion in a direction along the line portions 3342 (a direction parallel to the first hypothetical dividing line), which is also a direction lying along the X axis L1. Each of the upper electrode lines 335 connects to a common electrode line 336 which is disposed along the Y axis L2 between the first and third areas Ar1, Ar3 and the second and fourth areas Ar2, Ar4. In FIG. 3, the common electrode line 336 is disposed in proximity to the Y axis L2; however, optionally, it may be disposed on the Y axis L2.

Terminals connecting to the lower electrode lines 334 and the common electrode lines 336 are formed on the sensor substrate 20.

Specifically, as shown in FIG. 1, lower electrode terminals 351 are connected to each of the lower electrode lines 334 which lead out from the lower electrodes 331 of each of the ultrasonic transducers 30. A common electrode line terminal 361 is connected to the common electrode line 336.

As shown in FIG. 1, these terminals 351, 361 are disposed in dispersed fashion at three sides of the sensor substrate 20.

Therefore, in the present embodiment, the common electrode line 336 is disposed along the direction of the Y axis L2, i.e., the first direction, and is disposed between two columns composed of the plurality of ultrasonic transducers 30 along this first direction.

The lower electrode lines 334, which are the first electrode lines, are provided with the lead portions 3341 and the line portions 3342. The lead portions 3341 lead out in the first direction. The line portions 3342 are linear segments which extend along the X axis L1, i.e., the second direction.

The upper electrode lines 335, which are the second electrode lines of the ultrasonic transducers 30 situated in the first area Ar1 and the second area Ar2, connect to the common electrode line 336 between the proximal end thereof where it connects to the common electrode line terminal 361 and the distal end to the opposite side from this proximal end, and specifically, at locations between a point at midpoint and the distal end of the common electrode line 336.

The upper electrode lines 335, which are the second electrode lines of the ultrasonic transducers 30 situated in the third area Ar3 and the fourth area Ar4, connect at locations between the aforementioned point and the proximal end.

The lead portions 3341 which lead out from the lower electrodes 331, which are the first electrodes of the ultrasonic transducers 30 situated in the first area Ar1 and the second area Ar2, and the lead portions 3341 which lead out from the lower electrodes 331, which are the first electrodes of the ultrasonic transducers 30 situated in the third area Ar3 and the fourth area Ar4, lead out in directions away from one another, specifically, in the +Y axis direction and the −Y axis direction. In other words, in the first area Ar1, the second area Ar2, the third area Ar3 and the fourth area Ar4, the lead portions 3341 lead out in directions away from X axis.

Circuit Configuration of Ultrasonic Transducers

FIG. 4 is a circuit diagram showing the circuit configuration of the ultrasonic sensor 10 shown in FIG. 1.

As shown in FIG. 4, the ultrasonic sensor 10 is provided with the aforementioned sensor substrate 20 and transmitting/receiving circuit 40, and with a control circuit 60.

During transmission, the transmitting/receiving circuit 40 outputs a drive signal to the lower electrodes 331 of the ultrasonic transducers 30, and outputs ultrasound from the ultrasonic transducers 30. Here, because the ultrasonic transducers 30 are aligned in two dimensions in a two-dimensional array, by delaying the timing at which ultrasound is emitted from each of the ultrasonic transducers 30, it is possible to emit ultrasound in the form of a beam which propagates as a planar wave in a desired direction.

Additionally, by processing the reception signal which is output when the ultrasound beam that was emitted by each of the ultrasonic transducers 30 is reflected by a measured object and then received by each of the ultrasonic transducers 30, the transmitting/receiving circuit 40 is able to measure the time elapsed from ultrasound emission to ultrasound reception (Time of Flight (TOF) data) and sense the distance from the ultrasonic elements to the measured object.

The control circuit 60 controls the transmitting/receiving circuit 40 and operates the ultrasonic sensor 10 in either transmitting mode or receiving mode.

The ultrasonic sensor 10 of the first embodiment described above has the following effects.

(1) In situations where the ultrasonic transducers 30 are disposed in a two-dimensional array on the sensor substrate 20, the sensor substrate 20 is divided into four areas Ar1 to Ar4 by the X axis L1 and the Y axis L2 which are orthogonal to one another in plan view of the sensor substrate 20. In each of the areas Ar1 to Ar4, each of the lower electrode lines 334 which lead out from the lower electrodes 331 of the ultrasonic transducers 30 extends in a direction away from the substrate center point O.

Specifically, in two areas Ar1, Ar2 or Ar3, Ar4 lying to either side of the Y axis along the X axis, the lower electrode lines 334 do not lead out in the same direction across the Y axis. By virtue of this feature, the sensor substrate 20 is divided into the areas Ar1 to Ar4 by the X axis L1 and the Y axis L2, and the lower electrode lines 334 lead out within each of the areas Ar1 to Ar4, whereby the number of lower electrode lines 334 leading out between the ultrasonic transducers 30 within each of the areas Ar1 to Ar4 can be reduced.

(2) The sensor substrate 20 is divided into four areas by the X axis L1 and the Y axis L2 which are orthogonal to one another. Through quadripartite division, unlike a configuration having nine divisions as described previously, there is no formation of an area in the center section, and the number of lower electrode lines 334 leading out between the ultrasonic transducers 30 within each of the areas Ar1 to Ar4 can be reliably reduced, while complexity of lead out directions of the lower electrode lines 334 in association with an large number of divisions can be avoided.

(3) Because the X axis L1 and the Y axis L2 pass through the substrate center point O of the sensor substrate 20, the sensor substrate 20 can be divided equally into four areas Ar1 to Ar4. In so doing, it is possible to prevent bias in the number of lower electrode lines 334 between ultrasonic transducers 30 in the individual areas Ar1 to Ar4, so the numbers thereof can be equal. Consequently, whereas in situations where not all of the areas are equal in size, it is necessary to respectively modify the width of the spaces between the ultrasonic transducers 30 in individual areas, because the numbers of lines in each of the areas Ar1 to Ar4 are equal, the production steps for disposing the ultrasonic transducers 30 on the sensor substrate 20 can be simpler.

(4) The upper electrode lines 335 along the lower electrode lines 34 respectively connect to the common electrode line 336, and this common electrode line 336 is disposed only along the Y axis L2. Consequently, the number of common electrode lines can be greatly reduced as compared with the prior art, and configuration can be simpler. Also, because the common electrode line 336 is disposed along the Y axis L2, contact with the lower electrode lines 334 along the X axis L1 can be prevented.

(5) Between each of the ultrasonic transducers 30, the lead portions 3341 of the lower electrode lines 334 lead out in a direction orthogonal to the upper electrode lines 335, while the line portions 3342 extend parallel with respect to the upper electrode lines 335 from the distal ends of the lead portions 3341. The upper electrode lines 335 extend linearly in one direction. In so doing, by virtue of the lead portions 3341, the line portions 3342 extend parallel at locations away from the upper electrode lines 335, and therefore do not intersect the upper electrode lines 335. Consequently, shorting electrode pairs due to contact of the upper electrode lines 335 and the lower electrode lines 334 can be reliably prevented.

(6) The lead portions 3341 of the lower electrode lines 334 lead out in a direction away from the X axis L1, and therefore even in situations where common electrode lines 336 are disposed along both the X axis L1 and the Y axis L2, the lead portions 3341 and the common electrode lines 336 may be more reliably prevented from intersecting.

Second Embodiment

Figure 5:
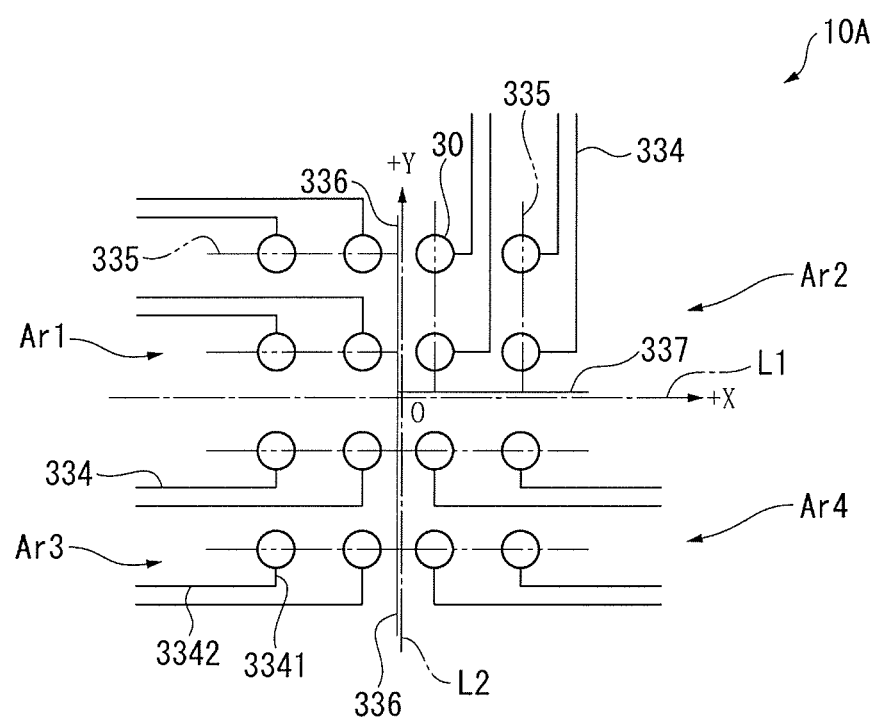
FIG. 5 is an enlarged plan view showing line construction of ultrasonic transducers according to a second embodiment of the present invention.

FIG. 5 is an enlarged plan view showing line construction of ultrasonic transducers 30 of an ultrasonic sensor 10A according to a second embodiment.

The second embodiment differs from the first embodiment in that, in the second area Ar2, the lower electrode lines 334, which are the first electrode lines, lead out towards the +Y direction. Specifically, in the second area Ar2, the Y axis direction is a direction parallel to the first hypothetical dividing line, and the X axis direction is a direction parallel to the second hypothetical dividing line. Configurations for the other areas Ar1, Ar3, and Ar4 are comparable to those of the first embodiment. In the present embodiment, two common electrode lines 336, 337 are provided, and the common electrode line 337 is situated along the X axis L1 between the second area Ar2 and the fourth area Ar4.

In the second area Ar2, the lead portions 3341 of the lower electrode lines 334 extend towards the +X direction along the X axis L1 (a direction parallel to the second hypothetical dividing line), and the line portions 3342 extend towards the +Y direction along the Y axis L2 (a direction parallel to the first hypothetical dividing line) from the distal ends of the lead portions 3341. Additionally, the upper electrode lines 335 extend along the Y axis direction (a direction parallel to the first hypothetical dividing line) and connect to the common electrode line 337 which is situated along the X axis L1 between the second area Ar2 and the fourth area Ar4.

Therefore, in the present embodiment, the direction along the Y axis L2 is the first direction, and the first common electrode line is constituted by the common electrode line 336 which is situated along this Y axis L2. The direction along the X axis L1 is the second direction, and the second common electrode line is constituted by the common electrode line 337 which is situated along this X axis L1.

Then, when partitioned by each of the common electrode lines 336, 337, the sensor substrate is divided into three areas. Specifically, in FIG. 5, the first area Ar1 and the third area Ar3 to the left side of the common electrode line 336 constitute a single area. The other two areas are the second area Ar2 to the right side of the common electrode line 336 and to the upper side of the common electrode line 337, and the fourth area Ar4 to the right side of the common electrode line 336 and to the lower side of the common electrode line 337.

In the present embodiment, the first area Ar1, the third area Ar3, and the fourth area Ar4 constitute first line pattern areas, and the second area Ar2 constitutes a second line pattern area.

In the first line pattern areas, the lower electrode lines 334, which are the first electrode lines, are provided with lead portions 3341 and with line portions 3342. The lead portions 3341 lead out in the first direction. The line portions 3342 are linear segments that lead out along the second direction.

The upper electrode lines 335, which are the second electrode lines, are situated along the second direction, and connect to the first common electrode line 336.

The second common electrode line 337 connects to the first common electrode line 336 at a location between the proximal end thereof which is connected to the common electrode terminal 361, and the distal end at an opposite side from this proximal end. The upper electrode lines 335 which are the second electrode lines of the ultrasonic transducers 30 that are situated in the first area Ar1 connect to the first common electrode line 336 at locations between the distal end and the point of connection of the second common electrode line 337.

The upper electrode lines 335 which are the second electrode lines of the ultrasonic transducers 30 that are situated in the third area Ar3 and the fourth area Ar4 connect to the first common electrode line 336 at locations between the proximal end and the point of connection of the second common electrode line 337.

The lead portions 3341 leading out from the lower electrodes 331 which are the first electrodes of the ultrasonic transducers 30 that are situated in the first area Ar1, and the lead portions 3341 leading out from the lower electrodes 331 which are the first electrodes of the ultrasonic transducers 30 that are situated in the third area Ar3 and the fourth area Ar4, lead out in directions away from one another, specifically, in the +Y axis direction and in the −Y axis direction. In other words, in the first area Ar1, the third area Ar3 and the fourth area Ar4, the lead portions 3341 lead out in directions away from X axis.

One of the first line pattern areas in FIG. 5 is an area that is bounded by the outside edge of the sensor substrate and by a first common electrode extension line representing an extension of the distal end of the first common electrode line 336 from the proximal end of the first common electrode line 336 to the sensor substrate outside edge, and that does not contain the second common electrode line 337 (the area to left side of the first common electrode line 336 in FIG. 5).

Another one of the first line pattern areas in FIG. 5 is an area that is bounded by the outside edge of the sensor substrate, by a segment of the first common electrode line 336 from the proximal end thereof to the connection point with the second common electrode line 337, and by a second common electrode extension line representing an extension of the distal end of the second common electrode line 337 from this connection point to the sensor substrate outside edge (the area to right side of the first common electrode line 336 and to the lower side of the second common electrode line 337 in FIG. 5).

The second line pattern area in FIG. 5 is an area that is bounded by the outside edge of the sensor substrate, by a segment of the first common electrode line from the connection point of the first common electrode line 336 and the second common electrode line 337 to a section of the first common electrode line 336 that on the distal end side thereof reaches to the sensor substrate outside edge, and by a second common electrode extension line representing an extension of the distal end of the second common electrode line 337 from this connection point to the sensor substrate outside edge (the area to right side of the first common electrode line 336 and to the upper side of the second common electrode line 337 in FIG. 5).

The ultrasonic sensor 10A of the second embodiment described above affords effects comparable to effects (1) to (6) of the preceding first embodiment, and permits various line layouts to be realized.

Third Embodiment

Figure 6:
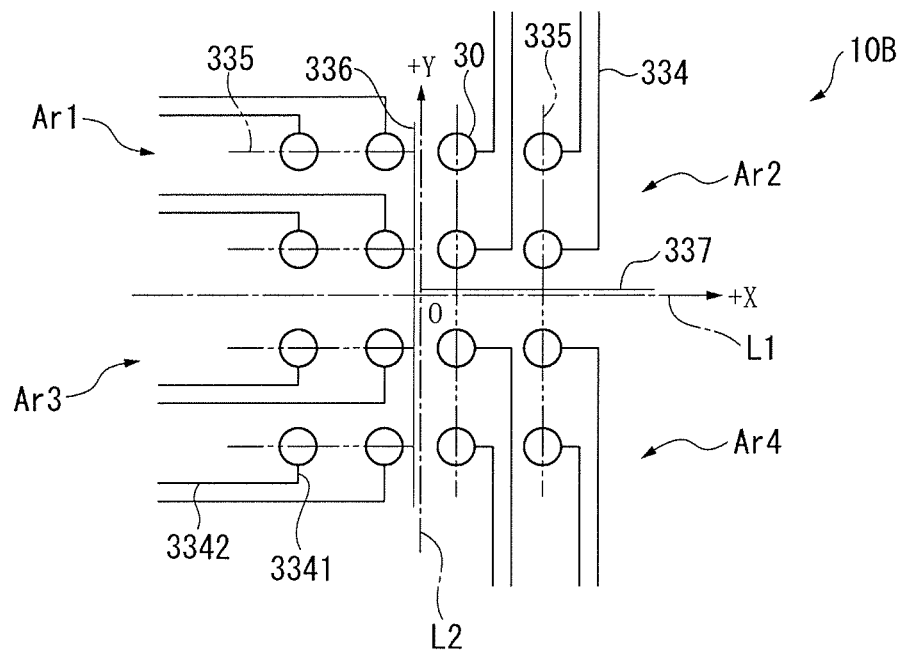
FIG. 6 is an enlarged plan view showing line construction of ultrasonic transducers according to a third embodiment of the present invention.

FIG. 6 is an enlarged plan view showing line construction of ultrasonic transducers 30 of an ultrasonic sensor 10B according to a third embodiment.

The present embodiment differs from the preceding second embodiment in terms of the line layout in the fourth area Ar4. Because the other areas Ar1 to Ar3 are similar in configuration to those in the second embodiment, a description is omitted here. In the present embodiment, as in the second embodiment, there are provided two common electrode lines, i.e., a first common electrode line 336 and a second common electrode line 337.

In the fourth area Ar4, the lead portions 3341 of the lower electrode lines 334 extend towards the +X axis direction along the X axis L1, and the line portions 3342 extend towards the −Y axis direction along the Y axis L2 from the distal ends of the lead portions 3341. The upper electrode lines 355 extend along the Y axis direction and are respectively connected to the common electrode line 337 which is situated along the X axis L1 between the second area Ar2 and the fourth area Ar4. Specifically, in the fourth area Ar4, the Y axis direction is a direction parallel to the first hypothetical dividing line, and the X axis direction is a direction parallel to the second hypothetical dividing line.

Therefore, in the present embodiment, the first area Ar1 and the third area Ar3 to the left side of the common electrode line 336 are first line pattern areas, and the second area Ar2 and the fourth area Ar4 are second line pattern areas.

The upper electrode lines 335 that are situated in the second area Ar2 and the fourth area Ar4 respectively connect to the second common electrode line 337 at locations between one end thereof and the connection point with the first common electrode line 336. Therefore, the lead portions 3341 of the lower electrode lines 334 that are situated in these areas Ar2, Ar4 lead out in the same direction (the +X axis direction).

The first line pattern areas in FIG. 6 are areas that are bounded by the outside edge of the sensor substrate and by a first common electrode extension line representing an extension of the distal end of the first common electrode line 336 from the proximal end of the first common electrode line 336 to the sensor substrate outside edge, and that do not contain the second common electrode line 337 (areas to the left side of the first common electrode line 336 in FIG. 6).

The second line pattern areas in FIG. 6 are areas that are bounded by the outside edge of the sensor substrate and by the first common electrode extension line, and that contain the second common electrode line 337 (areas to the right side of the first common electrode line 336 in FIG. 6).

The ultrasonic sensor 10B of the third embodiment described above affords effects comparable to effects (1) to (6) of the preceding first embodiment, and permits various line layouts to be realized.

Fourth Embodiment

Figure 7:
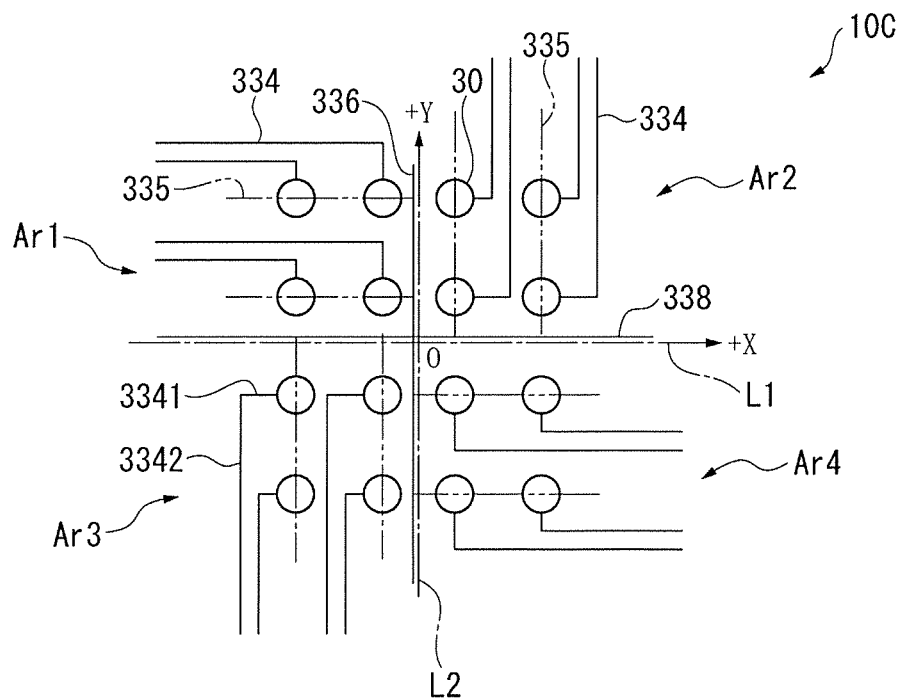
FIG. 7 is an enlarged plan view showing line construction of ultrasonic transducers according to a fourth embodiment of the present invention.

FIG. 7 is an enlarged plan view showing line construction of ultrasonic transducers 30 of an ultrasonic sensor 10C according to a fourth embodiment.

The present embodiment differs from the preceding second embodiment in terms of the line layout in the third area Ar3. Because the other areas Ar1, Ar3, Ar4 are similar in configuration to those in the second embodiment, a description is omitted here. In the present embodiment, there are provided two common electrode lines, i.e., a first common electrode line 336 and a second common electrode line 338, with the common electrode line 338 being situated along the X axis L1 between the first area Ar1 and the second area Ar2 on the one hand, and the third area Ar3 and the fourth area Ar4 on the other.

In the third area Ar3, the lead portions 3341 of the lower electrode lines 334 extend towards the −X direction along the X axis L1, and the line portions 3342 extend towards the −Y direction along the Y axis L2 from the distal ends of the lead portions 3341. The upper electrode lines 335 extend along the Y axis direction and are respectively connected to the common electrode line 338 which is situated along the X axis L1 between the first area Ar1 and the second area Ar2 on the one hand, and the third area Ar3 and the fourth area Ar4 on the other. Specifically, in the third area Ar3, the Y axis direction is a direction parallel to the first hypothetical dividing line, and the X axis direction is a direction parallel to the second hypothetical dividing line.

In the present embodiment, the common electrode lines 336 and 338 are situated between each of the areas Ar1 to Ar4, and therefore in each of the areas Ar1 to Ar4 the lead portions 3341 of the lower electrode lines 334 extend in directions away from either the X axis L1 or the Y axis L2, thereby preventing the lead portions 3341 from intersecting the common electrode line 336.

Therefore, in the present embodiment, the first area Ar1 and the fourth area Ar4 are first line pattern areas, and the second area Ar2 and the third area Ar3 are second line pattern areas.

The upper electrode lines 335 that are situated in the first area Ar1 and the fourth area Ar4 are respectively connected to the first common electrode line 336 at locations to the distal end side and to the proximal end side of the connection point of the first common electrode line 336 and the second common electrode line 338. Therefore, the lead portions 3341 of the lower electrode lines 334 that are situated in these areas Ar1, Ar4 lead out in directions away from one another (The +Y axis direction and the −Y axis direction). In other words, in the first area Ar1 and the fourth area Ar4, the lead portions 3341 lead out in directions away from X axis.

The upper electrode lines 335 that are situated in the second area Ar2 and the third area Ar3 are respectively connected to the second common electrode line 338 at locations to the one end side and to the other end side of the connection point of the first common electrode line 336 and the second common electrode line 338. Therefore, the lead portions 3341 of the lower electrode lines 334 that are situated in these areas Ar2, Ar3 lead out in directions away from one another (The +X axis direction and the −X axis direction). In other words, in the second area Ar2 and the third area Ar3, the lead portions 3341 lead out in directions away from Y axis.

The first line pattern areas in FIG. 7 are areas that, among four areas which are bounded by the outside edge of the sensor substrate, by a first common electrode extension line representing an extension of the distal end of the first common electrode line 336 from the proximal end of the first common electrode line 336 to the sensor substrate outside edge, and by a second common electrode extension line representing extensions of both ends of the second common electrode line 338 to reach the sensor substrate outside edge, are an area to the +Y axis side and the −X axis side of the connection point of the first common electrode line 336 and the second common electrode line 338 (an area to the left side of the first common electrode line 336 and the upper side of the second common electrode line 338 in FIG. 7), and an area to the −Y axis side and the +X axis side (an area to the right side of the first common electrode line 336 and the lower side of the second common electrode line 338 in FIG. 7).

The second line pattern areas in FIG. 7 are areas that, among four areas which are bounded by the outside edge of the sensor substrate, by the first common electrode extension line, and by the second common electrode extension line, are an area to the +Y axis side and the +X axis side of the connection point of the first common electrode line 336 and the second common electrode line 338 (an area to the right side of the first common electrode line 336 and the upper side of the second common electrode line 338 in FIG. 7), and an area to the −Y axis side and the −X axis side (an area to the left side of the first common electrode line 336 and the lower side of the second common electrode line 338 in FIG. 7).

The ultrasonic sensor 10C of the fourth embodiment described above affords effects comparable to effects (1) to (6) of the preceding first embodiment, and permits various line layouts to be realized.

Fifth Embodiment

Figure 8:
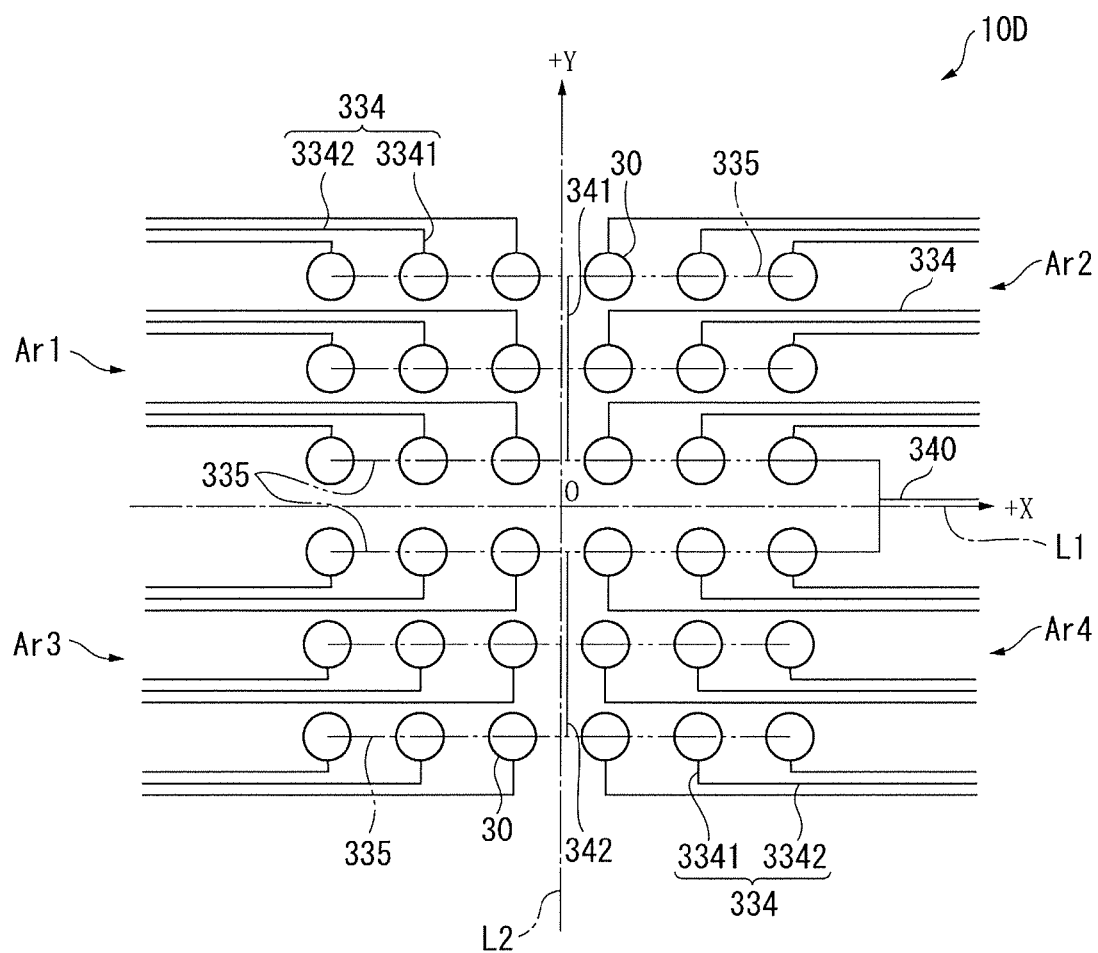
FIG. 8 is an enlarged plan view showing line construction of ultrasonic transducers according to a fifth embodiment of the present invention.

FIG. 8 is an enlarged plan view showing line construction of ultrasonic transducers 30 of an ultrasonic sensor 10D according to a fifth embodiment.

The present embodiment differs from the preceding first embodiment in terms of the line layout of the common electrode lines. Because the disposition layout of the ultrasonic transducers 30 and the line layout of the lower electrode lines 334 are similar in configuration to those in the first embodiment, a description is omitted here.

In the present embodiment, common electrode lines 340, 341, and 342 are provided. The common electrode line 340 is situated along the X axis L1, and splits into two branches which connect to each of the upper electrode lines 335 which are adjacent to the X axis L1. The common electrode lines 341 and 342 are situated along the Y axis L2.

The upper electrode lines 335 that are situated in the first area Ar1 and the second area Ar2 connect to the common electrode line 341.

The upper electrode lines 335 that are situated in the third area Ar3 and the fourth area Ar4 connect to the common electrode line 342.

The ultrasonic sensor 10D of the fifth embodiment described above affords effects comparable to effects (1) to (6) of the preceding first embodiment.

Further, because the common electrode line 340 can lead out in the direction of the X axis L1 in the same way as the lower electrode lines 334, the terminals of the lines in the ultrasonic sensor 10D can be concentrated at the two sides lying in the X axis direction of the sensor substrate 20.

Sixth Embodiment

Figure 9:
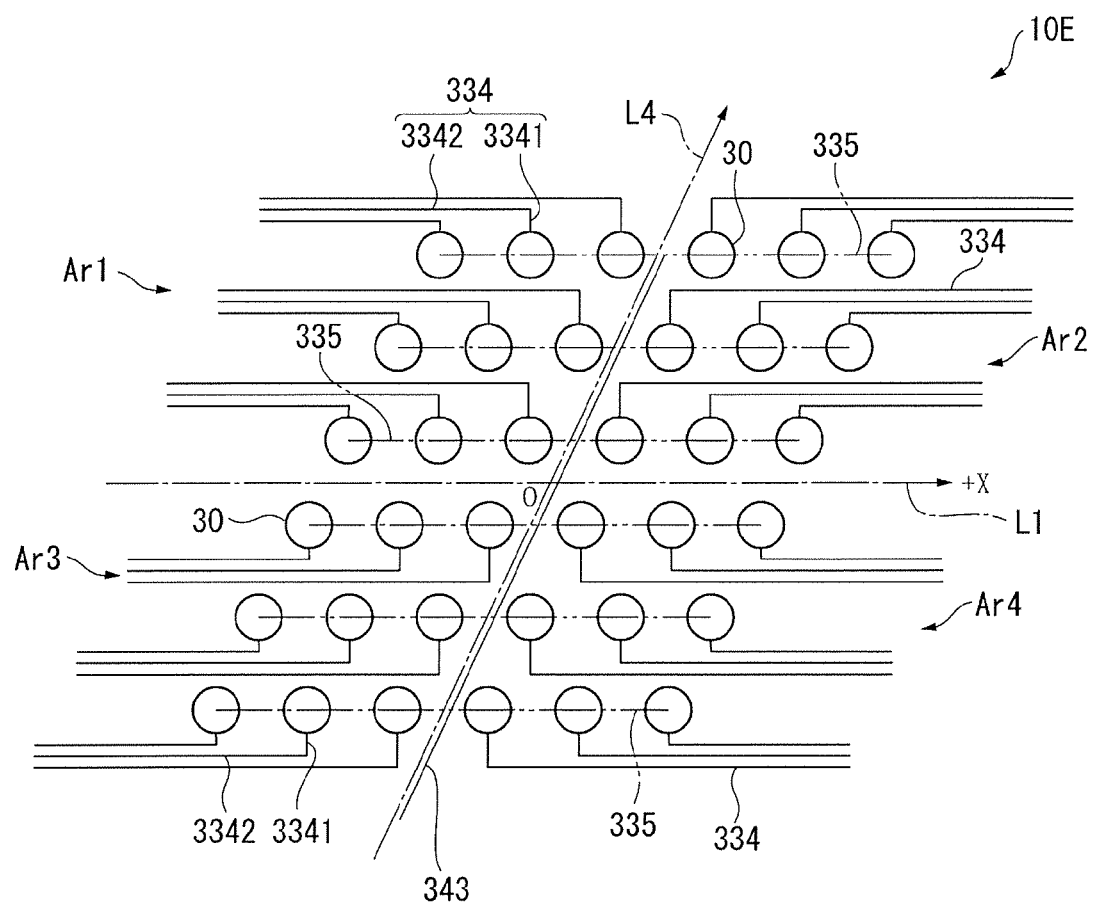
FIG. 9 is an enlarged plan view showing line construction of ultrasonic transducers according to a sixth embodiment of the present invention.

FIG. 9 is an enlarged plan view showing line construction of ultrasonic transducers 30 of an ultrasonic sensor 10E according to a sixth embodiment.

The present embodiment differs from the preceding first embodiment in terms of the disposition layout of the ultrasonic transducers 30 and the line layout of the common electrode lines.

In the first embodiment, the two hypothetical dividing lines were the X axis L1 and the Y axis L2 which are orthogonal to one another. In the present embodiment, however, of the two hypothetical dividing lines, while the first hypothetical dividing line is the X axis L1, the second hypothetical dividing line is not the Y axis L2, but rather an axis L4 which intersects the X axis L1 at a prescribed angle of less than 90 degrees. The tolerance angle of the axis L1 and L4 is set, for example, in a range of at least 60 degrees but less than 90 degrees.

The ultrasonic transducers 30 are disposed two-dimensionally along the X axis L1 and the axis L4.

In the present embodiment, a common electrode line 343 is provided along the axis L4. As in the first embodiment, the upper electrode lines 335 that are situated along the X axis L1 are connected to this common electrode line 343.

Because the line layout of the lower electrode lines 334 is similar in configuration to that in the first embodiment, a description is omitted here.

The ultrasonic sensor 10E of the sixth embodiment described above affords effects comparable to effects (1) to (6) of the preceding first embodiment.

Further, where the tolerance angle of the axis L1 and L4 is set to less than 90 degrees and the ultrasonic transducers 30 are aligned along each of the axes L1, L4, six ultrasonic transducers 30 can be disposed around a single ultrasonic transducer 30 so as to encircle it. Therefore, a so-called dense hexagonal disposition can be adopted, and various line layouts can be realized.

Seventh Embodiment

Figure 10:
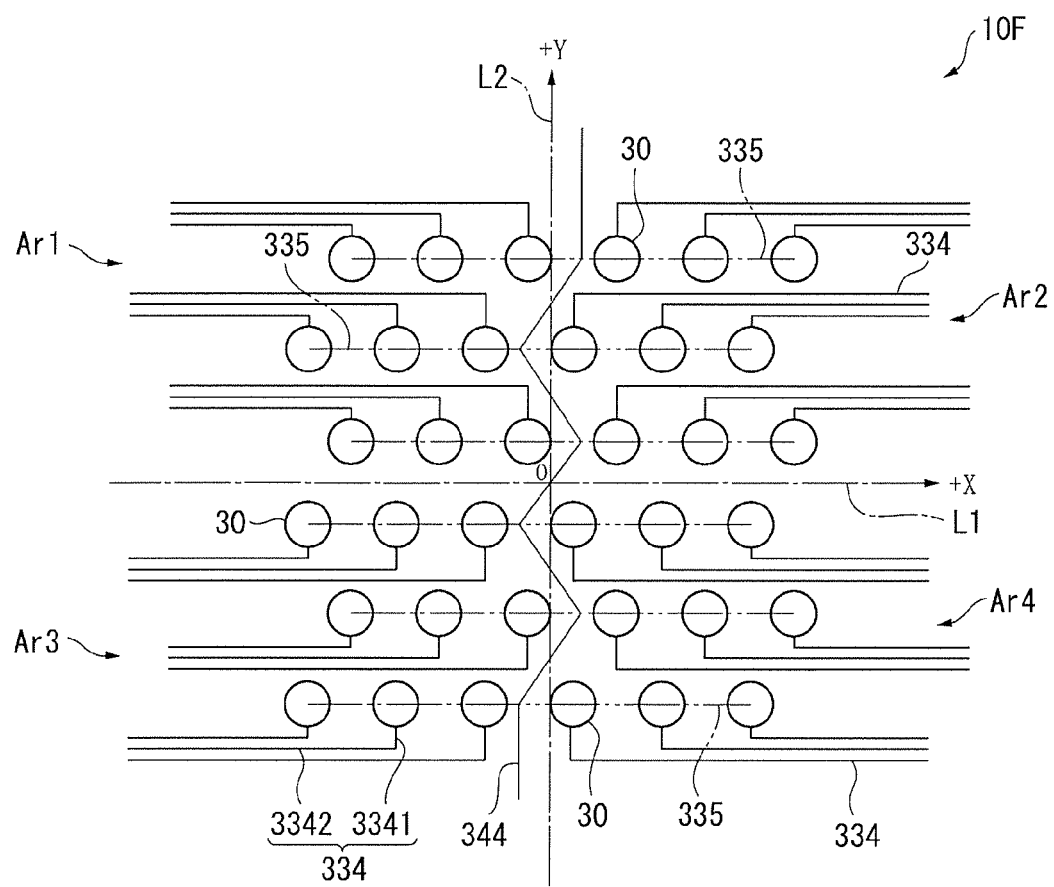
FIG. 10 is an enlarged plan view showing line construction of ultrasonic transducers according to a seventh embodiment of the present invention.

FIG. 10 is an enlarged plan view showing line construction of ultrasonic transducers 30 of an ultrasonic sensor 10F according to a seventh embodiment.

The present embodiment differs from the preceding first embodiment in terms of the disposition layout of the ultrasonic transducers 30 and the line layout of the common electrode lines.

In the first embodiment, the ultrasonic transducers 30 were disposed in matrix form along the X axis L1 and the Y axis L2. In the present embodiment, while the ultrasonic transducers 30 line up in the direction along the X axis L1, in the direction along the Y axis L2, each of the ultrasonic transducers 30 has a different position, creating a zigzag disposition. More specifically, the ultrasonic transducers 30 are disposed such that the positions of every other one are coincident in the Y axis L2 direction.

In the present embodiment, there is provided a common electrode line 344 which is disposed along the Y axis L2. The common electrode line 344 is routed along a zigzagging path between pairs of ultrasonic transducers 30 disposed to either side of the Y axis L2.

As in the first embodiment, the upper electrode lines 335 that are situated along the X axis L1 are connected to this common electrode line 344.

Because the line layout of the lower electrode lines 334 is similar in configuration to that in the first embodiment, a description is omitted here.

The ultrasonic sensor 10F of the seventh embodiment described above affords effects comparable to effects (1) to (6) of the preceding first embodiment.

Further, because the common electrode line 334 which is situated along the Y axis L2 is disposed in a zigzag arrangement, and each of the ultrasonic transducers 30 is also disposed in a zigzag arrangement, six ultrasonic transducers 30 can be disposed around a single ultrasonic transducer 30 to encircle the latter in a so-called dense hexagonal disposition, and various line layouts can be realized.

Eighth Embodiment

Figure 11:
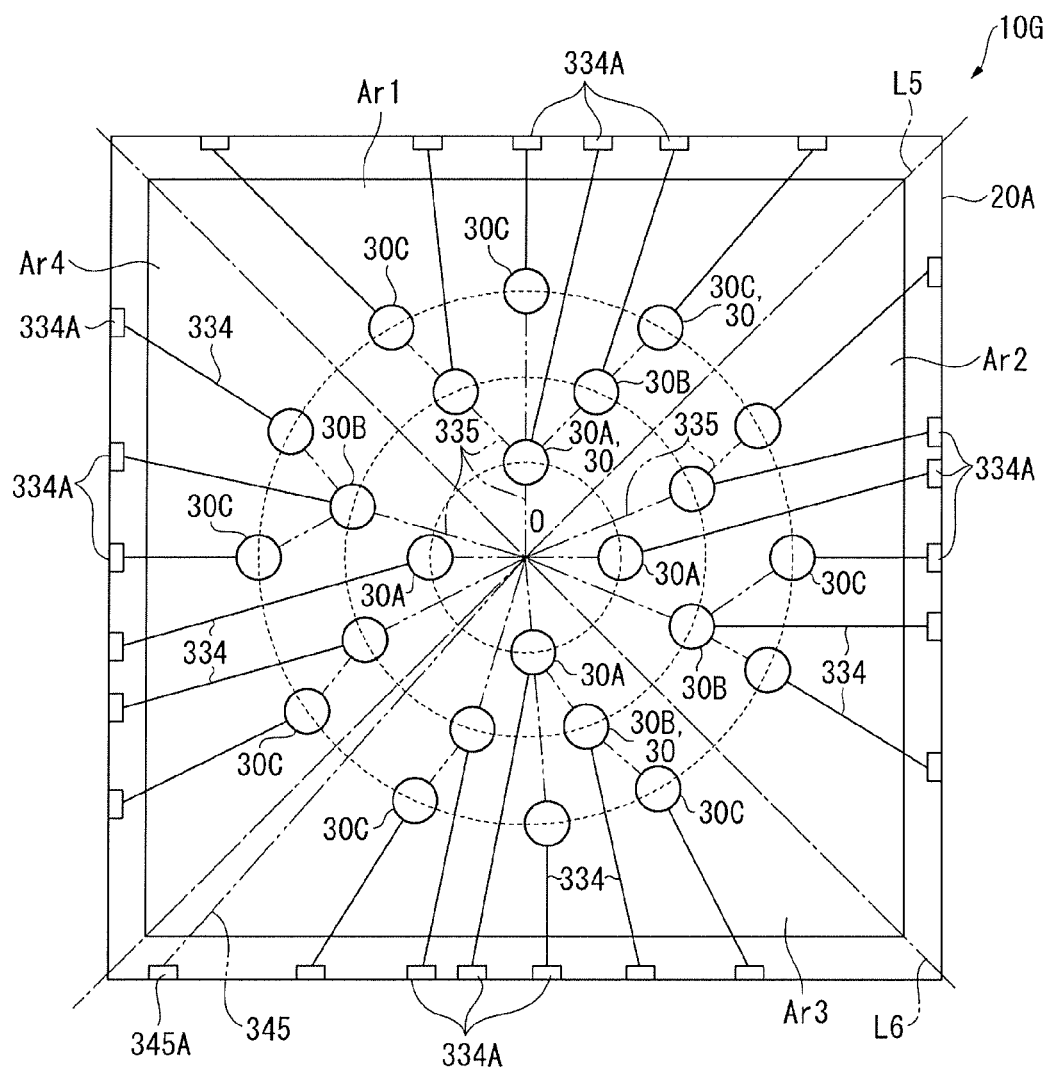
FIG. 11 is a plan view showing a general configuration of an ultrasonic sensor according to an eighth embodiment of the present invention.

FIG. 11 is a plan view showing a general configuration of an ultrasonic sensor 10G according to an eighth embodiment.

The present embodiment differs from the preceding embodiments in terms of the disposition layout of the ultrasonic transducers 30, and the line layouts of the common electrode lines, the upper electrode lines, and the lower electrode lines.

In the first embodiment, the ultrasonic transducers 30 were disposed in matrix form along the X axis L1 and the Y axis L2. In the present embodiment, the ultrasonic transducers 30 are disposed on three concentric circles which are centered on an intersection point O of axes L5 and L6 serving as an orthogonally-intersecting first hypothetical dividing line and second hypothetical dividing line.

The sensor substrate 20A of the ultrasonic sensor 10G is formed with a flat square shape. The sensor substrate 20A is divided into four areas Ar1, Ar2, Ar3, and Ar4 by the axes L5, L6 which are situated along the diagonals of the sensor substrate 20A.

Of the ultrasonic transducers 30 which are disposed on the three concentric circles, one ultrasonic transducer 30A for each of the areas Ar1, Ar2, Ar3, and Ar4, for a total of four, are disposed on the first circle closest to the intersection point O.

Two ultrasonic transducers 30B for each of the areas Ar1, Ar2, Ar3, and Ar4, for a total of eight, are disposed on the second circle from the intersection point O.

Further, three ultrasonic transducers 30C for each of the areas Ar1, Ar2, Ar3, and Ar4, for a total of twelve, are disposed on the third circle from the intersection point O.

Specifically, the number of the ultrasonic transducers 30A to 30C which are disposed on the concentric circles increases progressively moving away from the intersection point O.

In the present embodiment, there is provided a common electrode line 345 disposed along the axis L5 which is the first hypothetical dividing line. The common electrode line 345 is routed from a common electrode terminal 345A situated at the perimeter of the sensor substrate 20A to the aforementioned intersection point O, i.e., a location at the center of the ultrasonic transducers 30 which have been disposed in concentric circles.

The upper electrode lines 335 of the ultrasonic transducers 30A to 30C are connected to the end of the common electrode line 345 which is located at the intersection point O.

Specifically, the upper electrode lines 335 which lead out respectively from the four ultrasonic transducers 30A and the eight ultrasonic transducers 30B extend towards the intersection point O and connect directly to the common electrode line 345.

Further, the upper electrode lines 335 of the twelve outermost ultrasonic transducers 30C lead out towards the ultrasonic transducers 30A, 30B which are disposed to the inside thereof, and are connected to the upper electrode lines 335 of these ultrasonic transducers 30A, 30B.

The lower electrode lines 334 (first electrode lines) respectively lead out from the lower electrodes of each of the ultrasonic transducers 30A to 30C in directions away from the intersection point O. Therefore, lower electrode terminals 334A corresponding in number to the ultrasonic transducers 30A to 30C which are disposed in each of the areas Ar1 to Ar4 are situated at the four outer edges of the sensor substrate 20A.

Further, the number of lower electrode lines 334 which pass between the outermost ultrasonic transducers 30C is set to a maximum equal to the number of concentric circles. Because in the present embodiment the number of concentric circles is three, the number of lines passing through the outermost ultrasonic transducers 30C is set to three or fewer. As shown in FIG. 11, in the present embodiment, the number of lines passing through the ultrasonic transducers 30C is two at maximum.

The ultrasonic sensor 10G of the eighth embodiment described above affords effects comparable to effects (1) to (4) of the preceding first embodiment.

Further, the common electrode line 345 leads out along the axis L5 from the common electrode terminal 345A to the intersection point O, the upper electrode lines 335 of the ultrasonic transducers 30 lead out towards the intersection point O, and the lower electrode lines 334 lead to the outside peripheral part of the sensor substrate 20A in directions away from the intersection point O. Therefore, the common electrode line 345, the lower electrode lines 334, and the upper electrode lines 335 do not intersect one another, and the line layout can be designed easily.

Ninth Embodiment

Figure 12:
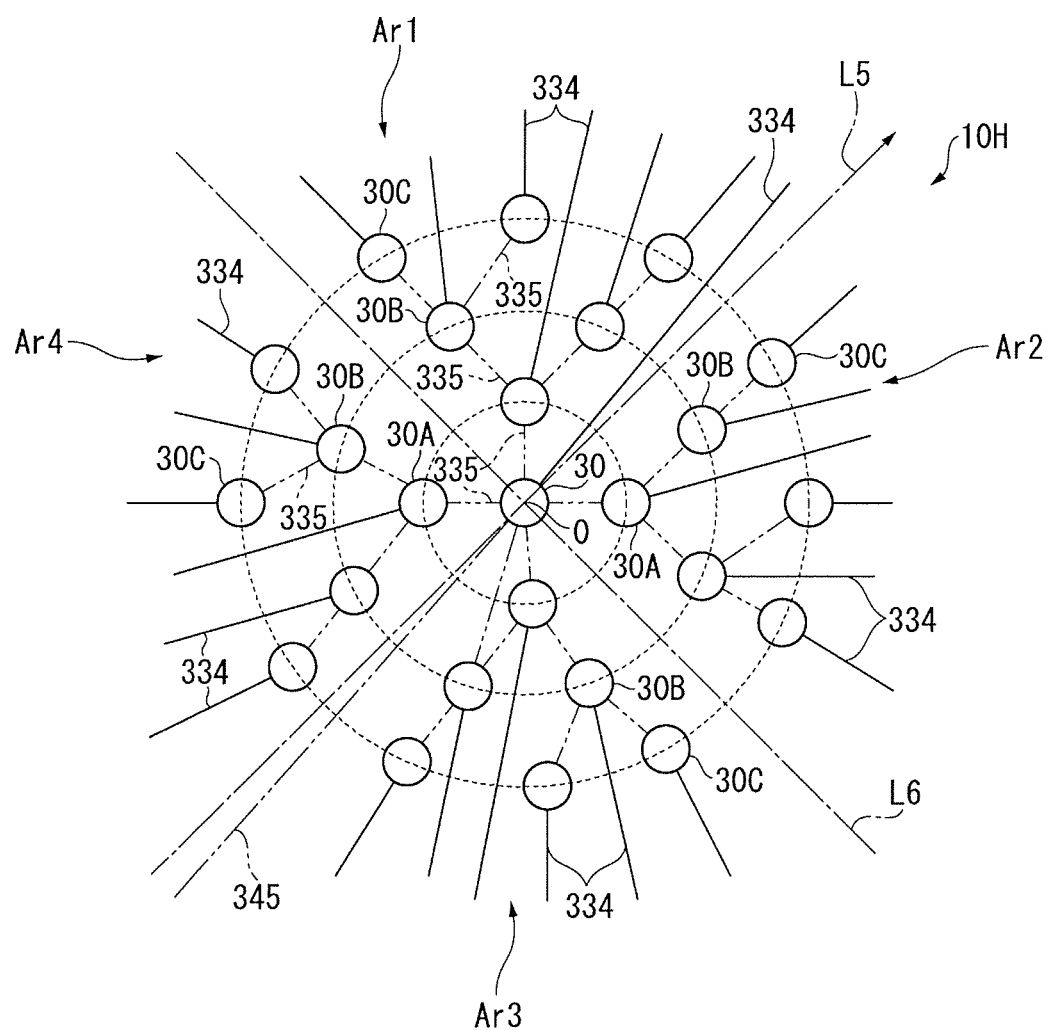
FIG. 12 is an enlarged plan view showing line construction of ultrasonic transducers according to a ninth embodiment of the present invention.

FIG. 12 is an enlarged plan view showing line construction of ultrasonic transducers 30 of an ultrasonic sensor 10H according to a ninth embodiment.

The present embodiment differs from the ultrasonic sensor 10G of the preceding eighth embodiment in terms of the line layout of the upper electrode lines 335, and in the feature that an ultrasonic transducer 30 is disposed at the location of the intersection point O.

In the present embodiment, upper electrode lines 335 which lead out from each of ultrasonic transducers 30A to 30C disposed on concentric circles connect to the upper electrode lines 335 of the ultrasonic transducers 30, 30A, 30B which are disposed on the next circle to the inside thereof.

Specifically, the upper electrode lines 335 that lead out from the outermost ultrasonic transducers 30C are connected to the upper electrode lines 335 of the ultrasonic sensors 30B on the second concentric circle from the intersection point O.

Also, the upper electrode lines 335 that lead out from the ultrasonic transducers 30B are connected to the upper electrode lines 335 of the ultrasonic sensors 30A on the first concentric circle from the intersection point O.

Further, the upper electrode lines 335 that lead out from the ultrasonic transducers 30A are connected to the upper electrode of the ultrasonic transducer 30 on the intersection point O.

A common electrode line 345 which is disposed along the axis L5 is connected to the upper electrode of the ultrasonic transducer 30 on the intersection point O.

Because the line layout of the lower electrode lines 334 of each of the ultrasonic transducers 30A to 30C is the same as in the eighth embodiment, a description is omitted here. The lower electrode line 334 of the ultrasonic transducer 30 that is disposed on the intersection point O also leads out in a direction away from the intersection point O.

Further, in the present embodiment, because an ultrasonic sensor 30 is disposed on the intersection point O as well, the number of lines passing between adjacent outermost ultrasonic transducers 30C is set to a maximum equal to the number of concentric circles plus 1. In the present embodiment, the number of concentric circles is 3, and therefore the number of lines passing between the outermost ultrasonic transducers 30C is set to 3+1=4 or fewer. As shown in FIG. 12, in the present embodiment, the number of lines passing between the outermost ultrasonic transducers 30C is two at maximum.

The ultrasonic sensor 10H according to the ninth embodiment affords effects comparable to those of the previous eighth embodiment.

Further, the common electrode line 345 leads out along the axis L5 from the common electrode terminal 345A to the intersection point O, and the upper electrode lines 335 of the ultrasonic transducers 30A to 30C are always connected to the ultrasonic transducers 30, 30A, 30B of the next circle to the inside. Therefore, line resistance from the common electrode terminal 354A of the common electrode line 345 to the upper electrodes of each of the ultrasonic transducers 30A to 30C can be substantially equal to that among the ultrasonic transducers 30A to 30C on the same given concentric circle.

Modifications of the Embodiments

While preferred configurations and methods for working the present invention have been disclosed above, there is no intention to limit the present invention to these.

In the above embodiments, the sensor substrate 20 was provided with four areas Ar1 to Ar4; however, optionally, the substrate may be divided into three areas, in which case the number of lower electrode lines 334 leading out between the ultrasonic transducers 30 in each of the areas can be smaller than the case where the substrate 20 is not divided. Optionally, the substrate may be divided into five or more areas, in which case the number of lower electrode lines 334 leading out between the ultrasonic transducers in each of the areas can be smaller than in the case of quadripartite division.

In the preceding first to seventh embodiments, in each of the areas Ar1 to Ar4, the lead out direction of the lower electrode lines 334 extended along the X axis or the Y axis, but the lines may extend in any direction that leads away from the substrate center point, such as extending in a diagonal direction, for example.

Figure 13A:
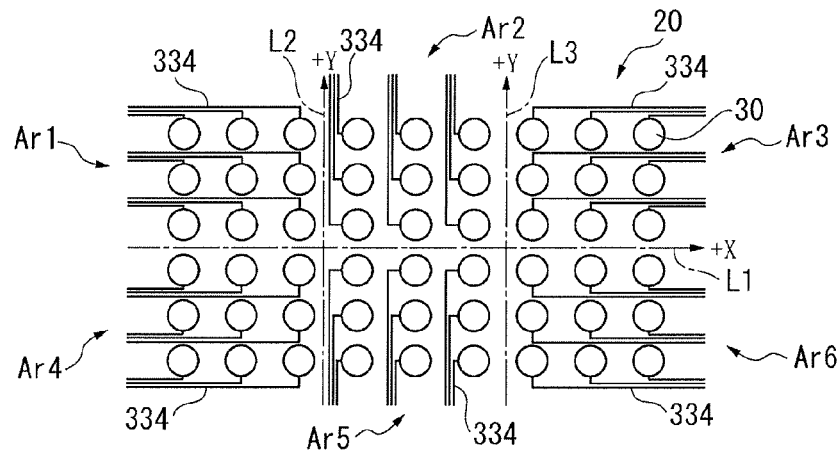
FIGS. 13A to 13C are plan views showing a modified example of line construction of an ultrasonic transducer.
Figure 13B:
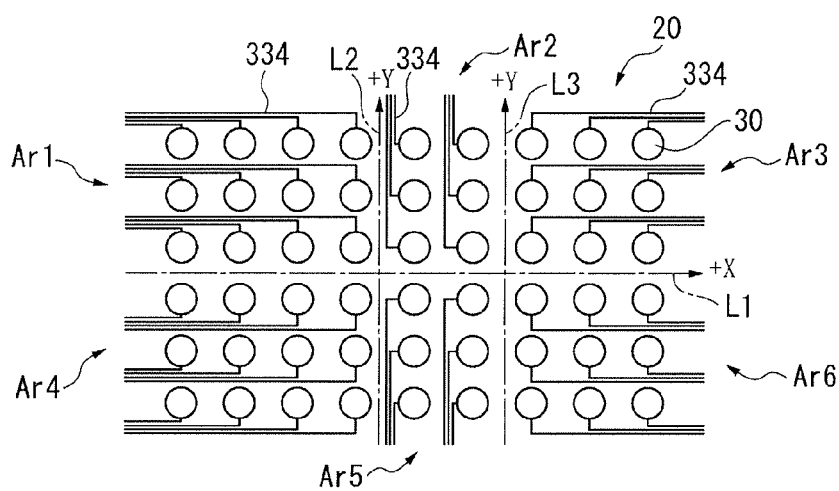
Figure 13C:
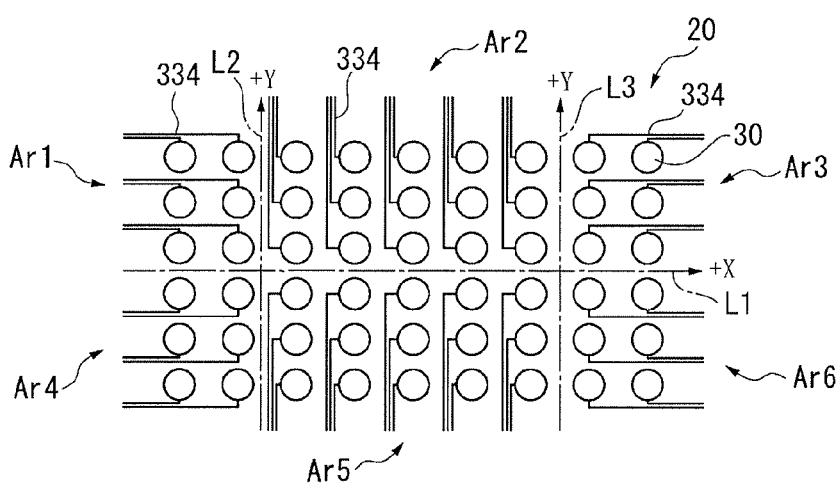

FIGS. 13A to 13C are diagrams showing a modified example of division into six areas as an example of division into five or more areas as discussed above.

In the present modified example, the sensor substrate 20 is divided into six by the X axis L1 and two Y axes L2, L3 to provide six areas Ar1 to Ar6.

In FIG. 13A, the areas Ar1 to Ar6 are uniformly divided such that each contains three rows and three columns.

With this configuration, in the second area Ar2 and the fifth area Ar5 in particular, because the lower electrode lines 334 do not cross over between areas, the lines necessarily extend along the Y axes L2, L3. Specifically, because the lower electrode lines 334 of the second area Ar2 do not extend along the X axis L1, the lines do not extend into the first area Ar1 or the third area Ar3, and the number of lower electrode lines 334 leading out between the ultrasonic transducers 30 in the first area Ar1 or the third area Ar3 can be reduced further. Likewise, for the fifth area Ar5 as well, the lower electrode lines 334 of the fifth area Ar5 do not extend into the fourth area Ar4 or the sixth area Ar6, and the number of lower electrode lines 334 leading out between the ultrasonic transducers 30 in the fourth area Ar4 or the sixth area Ar6 can be reduced further.

As shown in FIG. 13B, in a situation where the configuration of areas Ar3 and Ar6 is the same as in FIG. 13A, the areas Ar1 and Ar4 have a 3-row, 4-column configuration, and the areas Ar2 and Ar5 have a 3-row, 2-column configuration, the number of lower electrode lines 334 leading out between the ultrasonic transducers 30 in the areas Ar2 and Ar5 is three, which is the same as the number of lower electrode lines 334 leading out between the ultrasonic transducers 30 in the areas Ar2 and Ar5 in FIG. 13A.

In areas Ar1 and Ar4, however, the number of lower electrode lines 334 which extend in the X axis direction and lead out between the ultrasonic transducers 30 is four, which is a greater number of lines than in the case of FIG. 13A.

In a situation where, as shown in FIG. 13C, the areas Ar1, Ar3, Ar4, and Ar6 have a 3-row, 2-column configuration and the areas Ar2 and Ar5 have a 3-row, 5-column configuration, the number of lower electrode lines 334 leading out between the ultrasonic transducers 30 of the areas Ar2 and Ar5 is three, which is the same as in the configurations of FIGS. 13A and 13B; but in the areas Ar1, Ar3, Ar4, and Ar6, the number of lower electrode lines 334 extending in the X axis direction and leading out between the ultrasonic transducers 30 is two, which is a smaller number of lines as compared with the case of FIG. 13A or 13B. Specifically, where the configuration of ultrasonic sensors 30 shown in FIGS. 13A to 13C (6 rows, 9 columns) has been divided into upper and lower areas of three lines each by the X axis L1, through division at division locations in the column direction by the Y axis L2, L3 such that there are fewer than three columns in the areas Ar1, Ar3, Ar4, and Ar6, the number of lower electrode lines 334 extending in the X axis direction and leading out between the ultrasonic transducers 30 can be fewer than is the case in FIGS. 13A and 13B.

In FIG. 13C, the areas Ar1, Ar3, Ar4, and Ar6 have a 3-row, 2-column configuration however, optionally, either the areas Ar1 and Ar4 or the areas Ar3 and Ar6 may have a 3-row, 2-column configuration. In this case, according to the structure presented in FIGS. 13A and 13B, the lower electrode lines 334 leading out between the ultrasonic transducers 30 in either the areas Ar1 and Ar4 or the areas Ar3 and Ar6 can be fewer in number than in the structure illustrated in FIGS. 13A and 13B.

In the preceding embodiments, each of the areas Ar1 to Ar4 were divided equally at the substrate center point O; however, it is sufficient for the first hypothetical dividing line and the second hypothetical dividing line to simply divide the substrate into four areas, it not being necessary for the areas Ar1 to Ar4 to be divided equally.

In the preceding embodiments, the line layouts are merely exemplary, and the line layouts may be modified as appropriate for particular applications. In such situations, the configuration should be such that the lower electrode lines 334 in each of the areas do not cross over the axes L1 to L6 which constitute the first hypothetical dividing line and the second hypothetical dividing line.

In the preceding first to fourth embodiments, considerations pertaining to line layout necessitated that the common electrode line 336 be disposed along the Y axis L2, but, optionally, a common electrode line may be disposed along the X axis L1 only. For example, in the first embodiment above, the lower electrode lines 334 lead out in a direction along the X axis L1, but by instead leading out the lines in a direction along the Y axis L2, the upper electrode lines may connect to the common electrode line which is disposed along the X axis L1.

Figure 14:
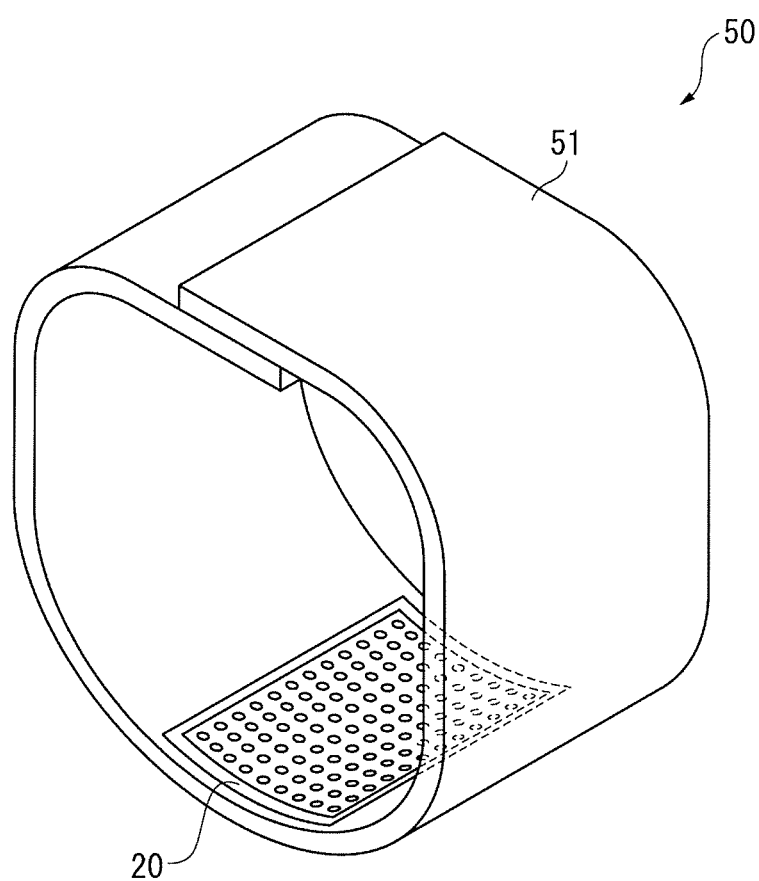
FIG. 14 is a general perspective view showing an example of a biometric measurement device as the electronic device of the present invention.

The ultrasonic sensor of the present invention may be incorporated into electronic devices such as biometric measurement devices for measuring blood flow or blood pressure. For example, as shown in FIG. 14, a biometric measurement device 50 may be devised by adhering the aforementioned sensor substrate 20 to the inside peripheral face of a band 51 which is intended to be wrapped around the arm, and additionally incorporating an IC or the like provided with a common electrode line of the sensor substrate 20, a transmitting/receiving circuit having electrical continuity with the lower electrode lines, and a control circuit for controlling this transmitting/receiving circuit.

In the process, in a situation where, as in the ultrasonic sensor 10 of the first embodiment, the lower electrode lines 334 which are the first electrode lines and the upper electrode lines 335 which are the second electrode lines are extended in the direction of the X axis L1 which represents the first hypothetical dividing line, while the common electrode line 336 is extended in the direction of the Y axis L2 which represents the second hypothetical dividing line, if the sensor substrate 20 is disposed such that the common electrode line 336 is routed along the direction of bending of the band 51, the lower electrode lines 334 and the upper electrode lines 335 will not bend, and therefore breakage of these electrode lines can be prevented. Due to the smaller number of common electrode lines 336, the lines can be formed thicker so as not to break if bent.

The electronic device is not limited to a biometric measurement device 50. The present invention may be incorporated, for example, into robots or automobiles, or implemented in proximity sensors or distance measurement sensors adapted to measure distance to or speed of a sensed object, in measurement sensors for non-destructive testing of pipelines or for monitoring flow rates of fluids in pipelines, in biometric testing devices adapted for ultrasound testing of conditions inside the body of biological system, or in any of various devices for measuring processes involving output and reception of ultrasound.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims.

Furthermore, the foregoing descriptions of the embodiments according to the present invention are provided for illustration only, and not for the purpose of limiting the invention as defined by the appended claims and their equivalents.

What is claimed is:

1. An ultrasonic sensor comprising:
a sensor substrate having a plurality of areas divided by at least two hypothetical dividing lines that intersect one another in plan view looking at the sensor substrate in a thickness direction;
a plurality of ultrasonic transducers disposed two-dimensionally on the sensor substrate so that each of the areas of the sensor substrate includes at least one of the ultrasonic transducers, each of the ultrasonic transducers having a first electrode; and
a plurality of first electrode lines having as origins thereof the first electrodes of the ultrasonic transducers, each of the first electrode lines having a linear segment extending, within each of the areas of the sensor substrate, in a direction away from an intersection point between the hypothetical dividing lines.

2. The ultrasonic sensor according to claim 1, wherein the linear segment of each of the first electrode lines within each of the areas extends along a prescribed direction.

3. The ultrasonic sensor according to claim 1, wherein each of the first electrode lines has, between the ultrasonic transducers,
a linear lead portion leading out from a corresponding one of the first electrodes of the ultrasonic transducers, and
a line portion corresponding to the linear segment, and extending from the lead portion along a straight line intersecting the lead portion.

4. The ultrasonic sensor according to claim 1, wherein the at least two hypothetical dividing lines include a first hypothetical dividing line and a second hypothetical dividing line which intersect one another in plan view looking at the sensor substrate in the thickness direction,
the ultrasonic transducers are two-dimensionally disposed in a direction parallel to the first hypothetical dividing line and a direction parallel to the second hypothetical dividing line,
the sensor substrate includes four areas divided by the first hypothetical dividing line and the second hypothetical dividing line, and
within each of the areas, the linear segment of each of the first electrode lines extends in the direction parallel to the first hypothetical dividing line.

5. The ultrasonic sensor according to claim 4, wherein the first hypothetical dividing line and the second hypothetical dividing line are orthogonal to one another.

6. The ultrasonic sensor according to claim 4, wherein each of the ultrasonic transducers has a second electrode, and
in each of the areas, a second electrode line that interconnects at least two of the second electrodes extends in the direction parallel to the first hypothetical dividing line with the second electrode line being connected to a common electrode line disposed along the second hypothetical dividing line.

7. The ultrasonic sensor according to claim 6, wherein the second electrode line extends linearly from each of the ultrasonic transducers in the direction parallel to the first hypothetical dividing line and interconnects each of the second electrodes of the ultrasonic transducers disposed in the direction parallel to the first hypothetical dividing line, and
between each of the ultrasonic transducers, each of the first electrode lines have
a lead portion leading out from a corresponding one of the first electrodes of the ultrasonic transducers in the direction parallel to the second hypothetical dividing line, and
a line portion extending from the lead portion in the direction parallel to the first hypothetical dividing line.

8. The ultrasonic sensor according to claim 7, wherein the lead portion of each of the first electrode lines has an origin at the corresponding one of the first electrodes, and extends in a direction away from the first hypothetical dividing line.

9. The ultrasonic sensor according to claim 1, further comprising
a common electrode line extending from an outside peripheral part of the sensor substrate along the first hypothetical dividing line to the intersection point of the first hypothetical dividing line and the second hypothetical dividing line,
the sensor substrate including four areas divided by the first hypothetical dividing line and the second hypothetical dividing line which intersect one another in plan view looking at the sensor substrate in the thickness direction,
each of the ultrasonic transducers having a second electrode, and being disposed at a location on one of a plurality of concentric circles centered on the intersection point of the first hypothetical dividing line and the second hypothetical dividing line,
each of the first electrode lines which leads out from the first electrode of each of the ultrasonic transducers extending, in each of the areas, to the outside peripheral part of the sensor substrate in a direction away from the intersection point of the first hypothetical dividing line and the second hypothetical dividing line, and
each of the second electrode lines which leads out from the second electrode of each of the ultrasonic transducers extending to an area inward of an outermost one of the concentric circles, and having a linear segment that extends in a direction approaching the intersection point of the first hypothetical dividing line and the second hypothetical dividing line.

10. The ultrasonic sensor according to claim 1, wherein the intersection point of the at least two hypothetical dividing lines lies at a substantially central point of the sensor substrate in plan view looking at the sensor substrate in the thickness direction.

11. An electronic device comprising the ultrasonic sensor according to claim 1.

12. An ultrasonic sensor comprising:
a sensor substrate;
a plurality of ultrasonic transducers, each of which having a first electrode and a second electrode and each of which being disposed two-dimensionally on the sensor substrate along a first direction and a second direction intersecting the first direction;
a common electrode line disposed along the first direction between columns of the ultrasonic transducers;
a plurality of first electrode lines each having as an origin each of the first electrodes of the ultrasonic transducers; and
a plurality of second electrode lines interconnecting the second electrodes of at least two of the ultrasonic transducers lined up in a direction parallel to the second direction, each of the first electrode lines having a linear segment extending in the direction parallel to the second direction and extending in a direction away from the common electrode line, and the second electrode lines extending along the second direction and connecting to the common electrode line.

13. The ultrasonic sensor according to claim 12, wherein each of the first electrode lines has a lead portion leading out in a direction parallel to the first direction from a corresponding one of the first electrodes of the ultrasonic transducers between each of the ultrasonic transducers, and a line portion corresponding to the linear segment, and extending from the lead portion along a straight line intersecting the lead portion.

14. The ultrasonic sensor according to claim 13, further comprising a common electrode terminal connected to the common electrode line, the second electrode lines being connected to the common electrode line at locations between a proximal end of the common electrode line connected to the common electrode terminal and a distal end of the common electrode line at an opposite side from the proximal end, and the lead portion leading out from each of the first electrodes of a first group extending away from a direction in which the lead portion leading out from each of the first electrodes of a second group extend, the first electrodes of the first group belonging to the ultrasonic transducers connected to a second group of the second electrode lines connected to the common electrode line at a location between a midpoint and the distal end of the common electrode line, the first electrodes of the second group belonging to the ultrasonic transducers connected to a second group of the second electrode lines connected to the common electrode line at a location between the midpoint and the proximal end of the common electrode line.

15. An ultrasonic sensor comprising:

a sensor substrate;

a plurality of ultrasonic transducers, each of which having a first electrode and a second electrode, and each of which being disposed two-dimensionally on the sensor substrate along a first direction and a second direction intersecting the first direction;

a first common electrode line extending in a direction parallel to the first direction, and being disposed between columns of the ultrasonic transducers; and a second common electrode line extending in a direction parallel to the second direction, being disposed between columns of the ultrasonic transducers, and being connected to the first common electrode line, at least one of a plurality of areas partitioned by the first common electrode line and the second common electrode line in plan view serving as a first line pattern area while the remaining area serving as a second line pattern area, in the first line pattern area, each of a plurality of first electrode lines having as origins thereof the first electrodes of the ultrasonic transducers having a linear segment extending in the direction parallel to the second direction and in a direction away from the first common electrode line, and a second electrode line interconnecting the second electrodes of at least two of the ultrasonic transducers that line up in the direction parallel to the second direction extending in the direction parallel to the second direction and being connected to the first common electrode line, and in the second line pattern area, each of a plurality of first electrode lines having as origins the first electrodes of the ultrasonic transducers having a linear segment extending in the direction parallel to the first direction and in a direction away from the second common electrode line, and a second electrode line interconnecting the second electrodes of at least two of the ultrasonic transducers that line up in the direction parallel to the first direction extending in the direction parallel to the first direction and being connected to the second common electrode line.

16. The ultrasonic sensor according to claim 15, wherein in the first line pattern area, each of the first electrode lines has a lead portion leading out from a corresponding one of the first electrodes of the ultrasonic transducers between the ultrasonic transducers in the direction parallel to the first direction, and a line portion corresponding to the linear segment, and extending from the lead portion along a straight line intersecting the lead portion, and in the second line pattern area, each of the first electrode lines has a lead portion leading out from a corresponding one of the first electrodes of the ultrasonic transducers between the ultrasonic transducers in the direction parallel to the second direction, and a line portion corresponding to the linear segment, and extending from the lead portion along a straight line intersecting the lead portion.

17. The ultrasonic sensor according to claim 16, further comprising a common electrode terminal connected to the first common electrode line, the second common electrode line being connected to the first common electrode line at a point between a proximal end of the first common electrode line connected to the common electrode terminal, and a distal end of the first common electrode line at an opposite side from the proximal end, and the lead portion leading out from each of the first electrodes of a first group extending away from a direction in which the lead portion leading out from each of the first electrodes of a second group extend, the first electrodes of the first group belonging to the ultrasonic transducers connected to the second electrode line connected to the first common electrode line at a location between the distal end and a point where the second common electrode line is connected to the first common electrode line, and the first electrodes of the second group belonging to the ultrasonic transducers connected to the second electrode line connected to the first common electrode line at a location between the proximal end and the point where the second common electrode line is connected to the first common electrode line.

18. The ultrasonic sensor according to claim 17, wherein the lead portion leading out from each of the first electrodes of a third group extends away from a direction in which the lead portion leading out from each of the first electrodes of a fourth group extend, the first electrodes of the third group belonging to the ultrasonic transducers connected to the second electrode line connected the second common electrode line at a location between one end of the second common electrode line and the point where the second common electrode line is connected to the first common electrode line, the first electrodes of the fourth group belonging to the ultrasonic transducers connected to the second electrode line connected to the second common electrode line at a location between another end of the second common electrode line and the point where the second common electrode line is connected to the first common electrode line.

* * * * *